US006433223B1

(12) United States Patent
Mikoshiba et al.

(10) Patent No.: US 6,433,223 B1
(45) Date of Patent: Aug. 13, 2002

(54) SILVER HALIDE PHOTOGRAPHIC MATERIAL AND HYDROXAMIC ACID-BASED COMPOUNDS USED THEREFOR

(75) Inventors: Hisashi Mikoshiba; Mamoru Sakurazawa; Masakazu Morigaki, all of Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/512,816

(22) Filed: Feb. 25, 2000

Related U.S. Application Data

(62) Division of application No. 08/710,516, filed on Sep. 18, 1996, now Pat. No. 6,057,090.

(30) Foreign Application Priority Data

Sep. 21, 1995 (JP) ........................................ 7-266203

(51) Int. Cl.[7] ........................................ C07C 229/00

(52) U.S. Cl. ........................ 562/621; 562/623; 562/567

(58) Field of Search .............................. 562/621, 567

(56) References Cited

U.S. PATENT DOCUMENTS

| | | | |
|---|---|---|---|
| 2,695,234 | A | 11/1954 | Hove et al. |
| 3,806,345 | A | 4/1974 | Willems et al. |
| 4,330,606 | A | 5/1982 | Sobel et al. |
| 4,339,515 | A | 7/1982 | Schranz et al. |
| 4,753,869 | A | 6/1988 | Long et al. |
| 5,206,131 | A | 4/1993 | Matsuda et al. |

FOREIGN PATENT DOCUMENTS

| | | |
|---|---|---|
| EP | 0698814 | 2/1996 |

*Primary Examiner*—Paul J. Killos
(74) *Attorney, Agent, or Firm*—Sughrue Mion, PLLC

(57) ABSTRACT

A silver halide photographic material is described, which contains the compound represented by the following formula (I):

(I)

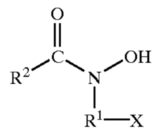

wherein $R^1$ represents a substituted or unsubstituted alkylene group having from 1 to 5 carbon atoms; X represents a water-soluble group; and R represents a substituted or unsubstituted alkyl group having the sum total of from 14 to 40 carbon atoms, an alkenyl group, an aryl group, an alkoxyl group, $-NR^3R^4$ ($R^3$ and $R^4$ each independently represents an alkyl group having from I to 40 carbon atoms, a hydrogen atom, or an aryl group), a bicycloalkyl group, a bicycloalkenyl group, a cycloalkyl group, a cycloalkenyl group or a heterocyclic group, provided that when X represents a quaternary ammonium salt structure, $R^2$ does not represent an alkyl group having from 14 to 17 carbon atoms.

1 Claim, No Drawings

SILVER HALIDE PHOTOGRAPHIC MATERIAL AND HYDROXAMIC ACID-BASED COMPOUNDS USED THEREFOR

This is a divisional of application Ser. No. 08/710,516 filed Sep. 18, 1996, now U.S. Pat. No. 6,057,090, the disclosure of which is incorporated herein by reference.

FIELD OF THE INVENTION

The present invention relates to a light-sensitive silver halide photographic material and, more particularly, to a photographic material which generates less fluctuation in photographic capabilities after storage and generates less fluctuation in photographic capabilities after photographing until development processing.

Further, the present invention relates to a silver halide photographic material which generates less fog.

Still further, the present invention relates to a novel hydroxamic acid based compound which provides photographically useful effect.

BACKGROUND OF THE INVENTION

In a silver halide color photographic material, it is required, as well as high sensitivity, that fluctuations in photographic characteristics are less during storage after manufacture of a photographic material and also after photographing until development processing.

Of the fluctuations in photographic characteristics after photographing until development processing, with respect to the prevention of latensification, a method by the combined use of a hardening agent having an active vinyl group with a triazine based compound is disclosed, for example, in JP-A-59-162546 (the term "JP-A" as used herein means an "unexamined published Japanese patent application").

However, the above method is not sufficient in the preventing effect and a further improvement has been desired.

On the other hand, in a full color photographic material, a multilayer structure comprising a plurality of emulsions having different spectral sensitivities is used to achieve the object of a full color photograph. However, although the emulsions for such a usage have been considerably improved, fog, intensification and fading of a latent image are liable to occur, therefore, they are not necessarily sufficient. 2-Hydroxyamino-1,3,5-triazines, for example, are useful for the improvement of such storage stabilities. However, the above storage stability improver used in each layer varies according to the emulsion used in each layer. Accordingly, a method to improve the storage stability of the latent image of the emulsion of rather a specific layer has been strongly desired in recent years.

Many of known 2-hydroxylamine-1,3,5-triazines are diffusible, therefore, these compounds have a drawback such that their function is exerted also to emulsions of layers other than the objective layer. On the other hand, hydroxamic acids having specific structures are disclosed in JP-A-59-198453 and JP-A-3-293666, but their use purposes are different from the object of the present invention and, further, their effect of the improvement of the storage stability of a latent image and the function to the emulsion of solely a specific layer are not sufficient. Accordingly, the development of a method to largely improve the storage stability of the latent image of only the objective layer has been strongly desired.

The present invention is to provide a method for improving the above-described storage stability of the emulsion and the stability of the latent image of a specific layer.

The present inventors have eagerly studied the method of improving the storage stability of an emulsion produced and the storage stability of a latent image to solve the above problems. As a result of various investigations particularly about the carbon atom number and the kind of substituents of storage stability improvers, a completely novel N-alkylhydroxamic acid based compound of the present invention which has a specific substituent and a carbon atom number has been discovered.

Further, it has been found that the compound of the present invention can achieve the objects of the present invention, when added to a silver halide photographic material, without changing the hue of the dye formed, affecting the dye-forming speed of a coupler, accelerating the decomposition of a coupler and the dye formed, deteriorating the film strength, or fogging an emulsion.

Still further, it has been found that the hydroxamic acid based compound according to the present invention shows a sufficient improving effect of the storage stability of a latent image and an emulsion with a reduced amount of addition.

Moreover, the compound according to the present invention is a completely novel compound which has not been known in the past. The photographic usefulness of this compound has become clear solely by the investigations of the present inventors.

SUMMARY OF THE INVENTION

One object of the present invention is to provide a compound which is very effective to improve the storage stability of a silver halide emulsion and the storage stability of a latent image and also to provide a method for improving the storage stability of a latent image using said compound.

Another object of the present invention is to provide a compound which can improve the storage stability of the latent image of solely a specific layer and also to provide a method for improving the storage stability of a latent image using said compound.

A further object of the present invention is to provide a compound which can improve the storage stability of a latent image without adversely affecting various photographic characteristics when added to a photographic material and also to provide a method for improving the storage stability of a latent image using said compound.

A still further object of the present invent on is to provide a compound which can achieve a sufficient improvement of the storage stability of a latent image and the storage stability of an emulsion with a reduced amount of addition.

The above objects of the present invention have been achieved by the following (1), (2) and (3).

(1) A silver halide photographic material which contains the compound represented by the following formula (I):

(I)

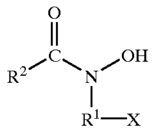

wherein $R^1$ represents a substituted or unsubstituted alkylene group having from 1 to 5 carbon atoms; X represents a water-soluble group; and R represents a substituted or unsubstituted alkyl group having the sum total of from 14 to 40 carbon atoms, an alkenyl group, an aryl group, an alkoxyl group, $—NR^3R^4$ ($R^3$ and $R^4$ each independently represents an alkyl group having from 1 to 40 carbon atoms, a hydrogen atom, or an aryl group), a bicycloalkyl group, a bicycloalkenyl group, a cycloalkyl group, a cycloalkenyl group or a heterocyclic group, provided that when X represents a quaternary ammonium salt structure, $R^2$ does not represent an alkyl group having from 14 to 17 carbon atoms.

(2) The silver halide photographic material described in the above (1), wherein $R^1$ represents a substituted or unsubstituted alkylene group having from 1 to 5 carbon atoms; and X represents a water-soluble group selected from the structures represented by the following formula (II), (III), (IV) or (V):

(II)

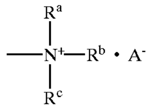

wherein $R^a$, $R^b$ and $R^c$, which may be the same or different, each independently represents a substituted or unsubstituted alkyl group having from 1 to 5 carbon atoms or a hydrogen atom; and $A^-$ represents a monovalent anion;

$$-SO_3^-.B^+ \qquad (III)$$

wherein $B^+$ represents a monovalent cation;

$$-(O-L)_n-O-R^d \qquad (IV)$$

wherein L represents a substituted or unsubstituted alkylene group having from 2 to 4 carbon atoms; n represents an integer of from 2 to 8; and $R^d$ represents a hydrogen atom, a substituted or unsubstituted alkyl group having prom 1 to 4 carbon atoms, or a substituted or unsubstituted aryl group having from 6 to 10 carbon atoms;

(V)

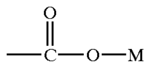

wherein M represents a hydrogen atom or a metal atom; and $R^2$, when X has the structure represented by formula (II), represents a substituted or unsubstituted alkyl group having the sum total of from 18 to 40 carbon atoms, a substituted or unsubstituted alkenyl group having the sum total of from 14 to 40 carbon atoms, a substituted or unsubstituted aryl group, a substituted or unsubstituted alkoxyl group, $-NR^3R^4$ which may be substituted ($R^3$ and $R^4$ each independently represents an alkyl group having from 1 to 40 carbon atoms, a hydrogen atom, or an aryl group), a substituted or unsubstituted bicycloalkenyl group, a substituted or unsubstituted bicycloalkyl group, a substituted or unsubstituted cycloalkyl group, a substituted or unsubstituted cycloalkenyl group or a substituted or unsubstituted heterocyclic group, and when X has the structure represented by formula (III), (IV) or (V), $R^2$ represents a substituted or unsubstituted alkyl group having the sum total of from 14 to 40 carbon atoms, a substituted or unsubstituted alkenyl group, a substituted or unsubstituted aryl group, a substituted or unsubstituted alkoxyl group, $-NR^3R$ which may be substituted ($R^3$ and $R^4$ each independently represents an alkyl group having from 1 to 40 carbon atoms, a hydrogen atom, or an aryl group), a substituted or unsubstituted bicycloalkenyl group, a substitutes or unsubstituted bicycloalkyl group, a substituted or unsubstituted cycloalkyl group, a substituted or unsubstituted cycloalkenyl group or a substituted or unsubstituted heterocyclic group.

(3) A compound represented by formula (VI):

(VI)

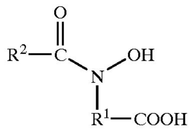

wherein $R^2$ represents a straight chain alkyl group having from 14 to 23 carbon atoms, a substituted aryl group having the sum total of from 20 to 50 carbon atoms, or a substituted alkyl group having the sum total of from 14 to 40 carbon atoms; and $R^1$ represents an unsubstituted alkylene group having from 1 to 3 carbon atoms.

DETAILED DESCRIPTION OF THE INVENTION

The compound represented by formula (I) will be explained in detail below.

In formula (I), $R^1$ represents a substituted or unsubstituted alkylene group having from 1 to 5 carbon atoms. When $R^1$ represents a substituted alkylene group, substituents thereof include, e.g., an alkyl group, an alkenyl group, an aryl group, a heterocyclic group, a halogen atom, an alkoxyl group, an aryloxy group, an alkylthio group, an arylthio group, a cyano group, a nitro group, an alkoxycarbonyl group, an aryloxycarbonyl group, a hydroxyl group, an acyl group, an acyloxy group, an alkyl- or arylsulfonyl group, an acylamino group, and an alkyl- or arylsulfonamido group.

The substituted alkylene group preferably has the sum total of from 1 to 10 carbon atoms.

Specific examples thereof include the following structures.

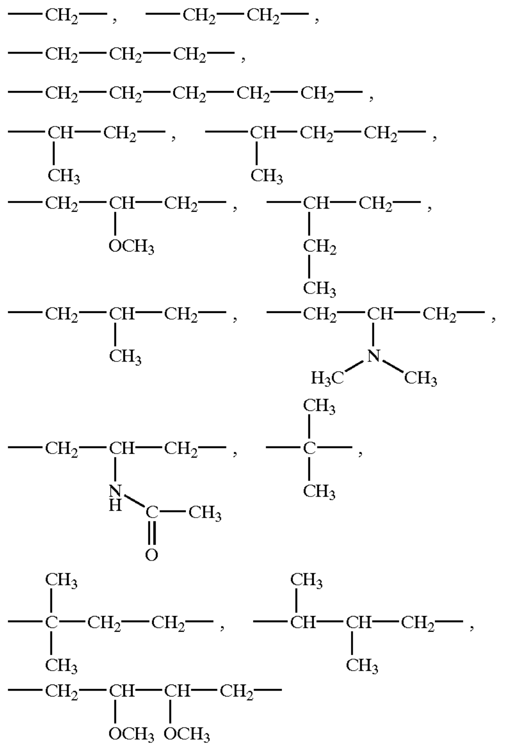

$R^1$ preferably represents an unsubstituted alkylene group, more preferably an unsubstituted alkylene group having from 1 to 3 carbon atoms, and still more preferably a methylene group.

X represents a water-soluble group. Examples of water-soluble groups include a carboxylic acid group (and the salts thereof), a sulfonic acid group (and the salts thereof), a quaternary ammonio group, a group having a polyether structure having at least 3 or more oxygen atoms, a group having a polyamine structure having at least 3 or more nitrogen atoms, a phosphoric acid residue, and a phosphorous acid residue.

Specific examples thereof include the following structures.

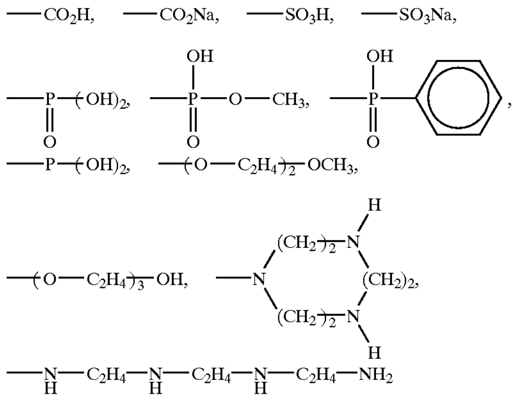

X preferably represents the structure represented by formula (II), (III), (IV) or (V).

In formula (II), $R^a$, $R^b$ and $R^c$, which may be the same or different, each independently represents a substituted or unsubstituted alkyl group having from 1 to 5 carbon atoms or a hydrogen atom, and preferably represents a substituted or unsubstituted alkyl group having from 1 to 5 carbon atoms.

The alkyl group used in the specification of the present invention includes a branched, straight chain, or cyclic alkyl group.

Further, the substituted alkyl group includes an alkyl group which has a heterocyclic structure by a substituent. For example, a 2-furyl group and a 2-piperidino group can be cited as examples of substituted alkyl groups.

Examples of substituents for substituted alkyl groups represented by $R^a$, $R^b$ and $R^c$ include a carboxyl group, a sulfo group, an aryl group, a cyano group, a nitro group, an arylcarbonyl group, an alkylcarbonyl group, a carbamoyl group, an alkoxycarbonyl group, an aryloxycarbonyl group, an acylamino group, an aryloxycarbonylamino group, an alkoxycarbonylamino group, an arylsulfonylamino group, an alkylsulfonylamino group, an aminocarbonylamino group, a sulfamoylamino group, $—NR^5R^6$ ($R^5$ and $R^6$, which may be the same or different, each independently represents an alkyl group, an aryl group or a hydrogen atom), an alkoxyl group, an aryloxy group, a heterocyclic oxy group, an alkylthio group, an arylthio group, a heterocyclic thio group, an alkylsulfonyl group, an arylsulfonyl group, a phosphoryl group, a halogen atom, a hydroxyl group, an acyloxy group, an alkenyl group and a heterocyclic group.

Of these, an alkoxyl group, an aryloxy group, an alkoxycarbonyl group, an aryloxycarbonyl group, a carbamoyl group, $—NR^5R^6$ ($R^5$ and $R^6$, which may be the same or different, each independently represents an alkyl group, an aryl group or a hydrogen atom), and an aryl group are preferred as substituents.

Specific examples of substituents will be described in detail in the explanation of $R^2$ below.

Specific examples of $R^a$, $R^b$ and $R^c$ include methyl, ethyl, isopropyl, n-butyl, n-propyl, n-heptyl, 2-cyanoethyl, 2-chloroethyl, and 3-methoxypropyl.

The case where all of $R^a$, $R^b$ and $R^c$ represent the same substituents is preferred to the case where $R^a$, $R^b$ and $R^c$ each represents different substituents.

The case where all of $R^a$, $R^b$ and $R^c$ represent unsubstituted alkyl groups having from 1 to 5 carbon atoms is more preferred.

$A^-$ represents a monovalent anion. Specific examples thereof include a chlorine anion, a bromine anion, an iodine anion, an acetic acid anion, and a p-toluenesulfonic acid anion. A ½ part of a divalent anion and a ⅓ part of a trivalent anion nay also be included. Specific examples thereof include a ½ sulfuric acid dianion, a ½ oxalic acid dianion, and a ⅓ phosphoric acid trianion.

Of these, A preferably represents a chlorine anion or a bromine anion.

Preferred structure of formula (II) is such that $R^a$, $R^b$ and $R^c$ all represent unsubstituted alkyl groups having from 1 to 5 carbon atoms and A represents a chlorine ion. More preferably, $R^a$, $R^b$ and $R^c$ all represent methyl groups and $A^-$ represents a chlorine ion.

In formula (III), $B^+$ represents a monovalent cation.

Specific examples thereof include a sodium cation, a potassium cation, and a lithium cation. A ½ part of a divalent cation may also be included. Specific examples thereof include a ½ calcium dication and a ½ magnesium dication. Further, quaternary ammonium may also be included.

Of these, $B^+$ preferably represents a sodium cation or a potassium cation.

In formula (IV), L represents a substituted or unsubstituted alkylene group having from 2 to 4 carbon atoms. Substituents described in $R^a$, $R^b$ and $R^c$ can be cited as substituents thereof.

L preferably represents an unsubstituted alkylene group having from 2 to 4 carbon atoms, and most preferably an ethylene group.

n represents an integer of from 2 to 8, preferably from 2 to 5, and most preferably 3.

$R^d$ represents a hydrogen atom, a substituted or unsubstituted alkyl group having from 1 to 4 carbon atoms, or a substituted or unsubstituted aryl group having from 6 to 10 carbon atoms.

When $R^d$ represents a substituted alkyl group, those described as substituents when $R^a$, $R^b$ and $R^c$ each represents a substituted alkyl group can be cited as substituents of the substituted alkyl group. When $R^d$ represents an alkyl group, an unsubstituted alkyl group is preferred to a substituted alkyl group.

When $R^d$ represents an alkyl group, specific examples thereof include methyl, ethyl, n-propyl, isopropyl, t-butyl, n-butyl, 2-cyanoethyl and 2-chloroethyl.

When $R^d$ represents an alkyl group, a methyl group is most preferred.

When $R^d$ represents a substituted aryl group, those described as substituents when $R^a$, $R^b$ and $R^c$ each represent a substituted aryl group can be cited as substituents of the substituted aryl group.

When $R^d$ represents an aryl group, an unsubstituted aryl group is preferred to a substituted aryl group.

Specific examples of aryl groups include phenyl, p-methoxyphenyl, and o-chlorophenyl.

When $R^d$ represents an aryl group, a phenyl group is most preferred.

It is preferred for $R^d$ to represent an alkyl group to an aryl group.

$R^d$ most preferably represents a methyl group.

Preferred structure of formula (IV) is such that L represents an unsubstituted alkylene group having from 2 to 4 carbon atoms, n represents from 2 to 5 and $R^d$ represents an unsubstituted alkyl group having from 1 to 4 carbon atoms.

The most preferred structure of formula (IV) is such that L represents an ethylene group, n represents 3 and $R^d$ represents a methyl group.

In formula (V), M represents a hydrogen atom or a metal atom. When M represents a metal atom, formula (V) becomes —CO—$O^-$ $M^+$. $M^+$ represents a monovalent metal cation, and examples thereof include those cited as specific examples of $B^+$in formula (III). Above all, a potassium ion and a sodium ion are preferred.

Of the structures represented by formula (II), (III), (IV) or (V), X is preferably represented by formula (V) and, above all, the case where M represents a hydrogen atom is preferred.

$R^2$ in formula (I) is described below.

When X is the structure represented by formula (II), $R^2$ represents a substituted or unsubstituted alkyl group having the sum total of from 18 to 40 carbon atoms, an alkenyl group having the sum total of from 14 to 40 carbon atoms, an aryl group, an alkoxyl group, —$NR^3R^4$ ($R^3$ and $R^4$ each independently represents an alkyl group having from 1 to 40 carbon atoms, a hydrogen atom, or an aryl group), a bicycloalkenyl group, a bicycloalkyl group, a cycloalkyl group, a cycloalkenyl group or a heterocyclic group.

When X is the structure represented by formula (III), (IV) or (V), $R^2$ represents a substituted or unsubstituted alkyl group having the sum total of from 14 to 40 carbon atoms, an alkenyl group, an aryl group, an alkoxyl group, —$NR^3R^4$ ($R^3$ and $R^4$ each independently represents an alkyl group having from 1 to 40 carbon atoms, a hydrogen atom, or an aryl group), a bicycloalkenyl group, a bicycloalkyl group, a cycloalkyl group, a cycloalkenyl group or a heterocyclic group.

The alkyl group is a substituted or unsubstituted straight chain or branched alkyl group.

When the alkyl group is an unsubstituted straight chain alkyl group, the alkyl group preferably has from 15 to 30 carbon atoms. Specific examples thereof include palmityl, eicosyl and docosyl.

When the alkyl group is an unsubstituted branched alkyl group, the alkyl group preferably has from 17 to 30 carbon atoms. Specific examples thereof include the following structures:

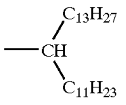

-continued

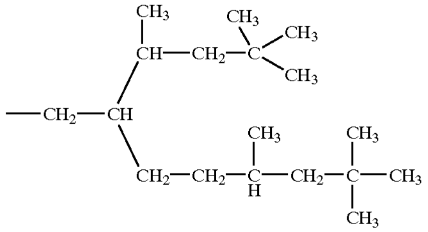

When X is represented by formula (II) and $R^2$ represents an unsubstituted alkyl group, $R^2$ preferably has from 18 to 30 carbon atoms. Further, when X is represented by formula (III), (IV) or (V) and R represents an unsubstituted alkyl group, $R^2$ preferably has from 15 to 30 carbon atoms.

When $R^2$ represents a substituted alkyl group, those described as substituents when $R^a$, $R^b$ and $R^c$ each represents a substituted alkyl group can be cited as substituents of the substituted alkyl group.

$R^2$ in formula (I) will be further described in detail. When $R^2$ represents a substituted alkyl group, preferred examples of substituents thereof include an alkoxyl group (an alkoxyl group having from 1 to 39 carbon atoms, e.g., methoxy, ethoxy, n-propoxy, isopronaoxy, n-pentoxy, n-hexyloxy, n-otyloxy, n-butoxy, stearyloxy, dodecyloxy, eicosyloxy, docosyloxy), in addition to the above, alkoxyl groups derived from higher alcohols such as Fine Oxocol 140, 1600, 1800, 180, 180N, 2000 and 2600 (trade names, produced by Nissan Chemical Industries, Ltd.) can also be included in specific examples of alkoxyl groups; an aryloxy group (an aryloxy group having from 6 to 39 carbon atoms, e.g., phenoxy, p-methoxyphenoxy, m-octyloxyphenoxy, o-chlorophenoxy, 2,4-di-t-octylphenoxy); an alkoxycarbonyl group (an alkoxycarbonyl group having from 2 to 39 carbon atoms, e.g., methoxycarbonyl, ethoxycarbonyl, n-butoxycarbonyl, isopropoxycarbonyl, t-butoxycarbonyl, n-octyloxycarbonyl, n-dodocyloxycarbonyl, pentadecyloxycarbonyl, stearyloxycarbonyl, oleyloxycarbonyl, docosyloxycarbonyl), in addition to the above, alkoxycarbonyl groups derived from higher alcohols such as Fine Oxocol 140, 1600, 1800, 180, 180N, 2000 and 2600 (trade names, produced by Nissan Chemical Industries, Ltd.) can also be included in specific examples of alkoxycarbonyl groups; an aryloxycarbonyl group (an aryloxycarbonyl group having from 6 to 39 carbon atoms, e.g., phenoxycarbonyl, p-ethoxyphenoxycarbonyl, m-dodecyloxyphenoxycarbonyl o-chlorophenoxycarbonyl, 2,4-di-t-octylphenoxycarbonyl); a carbamoyl group (a carbamoyl group having from 3 to 39 carbon atoms, e.g., dimethylcarbamoyl, diethylcarbamoyl, dioctylcarbamoyl, distearylcarbamoyl, dioleylcarbamoyl, bis(2-ethylhexyl) carbamoyl, stearyloxypropylcarbamoyl); and —$NR^5R^6$ (—$NR^5R^6$ having from 1 to 39 carbon atoms, e.g., octylamino, dioctylamino, stearylamino, distearylamino, oleylamino, dioleylamino, methylamino, anilino).

When $R^2$ represents a substituted alkyl group, the sum total of the carbon atom number is preferably from 14 to 35, more preferably from 18 to 30.

When $R^2$ represents an alkyl group, an unsubstituted straight chain alkyl group having from 18 to 30 carbon atoms is most preferred.

When $R^2$ represents an alkenyl group, the sum total of the carbon atom number is preferably from 18 to 34. A specific example of the unsubstituted alkenyl group includes the following structure:

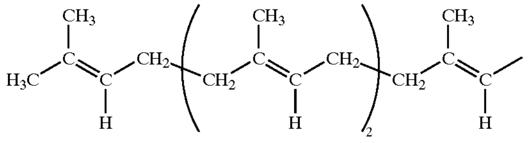

Further, specific examples of substituted alkenyl groups include the following structures:

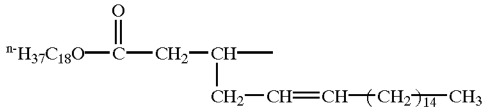

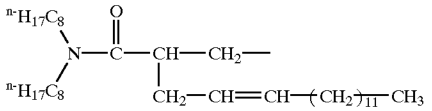

When $R^2$ represents an aryl group, the sum total of the carbon atom number is from 14 to 40, preferably from 18 to 35.

When $R^2$ represents an aryl group, a substituted aryl group is preferred to an unsubstituted aryl group. Examples of substituents of the aryl group include a carboxyl group, a sulfo group, an aryl group, a cyano group, a nitro group, an arylcarbonyl group, an alkylcarbonyl group, a carbamoyl group, an alkoxycarbonyl group, an aryloxycarbonyl group, an acylamino group, an aryloxycarbonylamino group, an alkoxycarbonylamino group, an arylsulfonylamino group, an alkylsulfonylamino group, an aminocarbonylamino group, a sulfamoylamino group, —$NR^5R^6$ ($R^5$ and $R^6$, which may be the same or different, each independently represents an alkyl group, an aryl group or a hydrogen atom), an alkoxyl group, an aryloxy group, a heterocyclic oxy group, an alkylthio group, an arylthio group, a heterocyclic thio group, an alkylsulfonyl group, an arylsulfonyl group, a phosphoryl group, a halogen atom, a hydroxyl group, an acyloxy group, an alkenyl group, an alkyl group and a heterocyclic group.

Of these, an arylcarbonyl group, an alkyl group, an alkylcarbonyl group, a carbamoyl group, an acylamino group, an arylsulfonylamino group, an alkylsulfonylamino group and an alkoxyl group are preferred.

Specific examples thereof include an arylcarbonyl group (an arylcarbonyl group having from 7 to 34 carbon atoms, e.g., benzoyl, p-toluyl, m-chlorobenzoyl, o-methoxybenzoyl, p-octyloxybenzoyl, m-stearoylaminobenzoyl), an alkylcarbonyl group (an alkylcarbonyl group having from 2 to 34 carbon atoms, e.g., acetyl, n-propionyl, pivaloyl, n-octylcarbonyl, n-stearoyl, n-lauroyl, 2-methoxyoctylcarbonyl), a carbamoyl group (a carbamoyl group having from 1 to 34 carbon atoms, e.g., methylcarbamoyl, dimethylcarbamoyl, isobutylcarbamoyl, cyclohexylcarbamoyl, n-octylcarbamoyl, di-n-octylcarbamoyl, oleylcarbamoyl, dimyristylcarbamoyl, N-methyl-N-phenylcarbonyl), an acylamino group (an acylamino group having from 2 to 34 carbon atoms, e.g., acetylamino, pivaloylamino, propionylamino, stearoylamino, lauroylamino, benzoylamino, p-stearyloxybenzoylamino), an arylsulfonylamino group (an arylsulfonylamino group having from 6 to 34 carbon atoms, e.g., benzenesulfonylamino, toluenesulfonylamino, p-bromobenzenesulfonylamino), an alkylsulfonylamino group (an alkylsulfonylamino group having from 1 to 34 carbon atoms, e.g., methanesulfonylamino, ethanesulfonylamino, n-butanesulfonylamino, n-octanesulfonylamino), an alkyl group (an alkyl group having from 1 to 18 carbon atoms, e.g., methyl, ethyl, t-butyl, t-octyl), and an alkoxyl group (an alkoxyl group having from 1 to 34 carbon atoms, e.g., methoxy, ethoxy, isopropoxy, octyloxy, stearyloxy), in addition to the above, alkoxyl groups derived from higher alcohols such as Fine Oxocol 140, 1600, 1800, 180, 180N, 2000 and 2600 (trade names, produced by Nissan Chemical Industries, Ltd.) can also be included in specific examples of alkoxyl groups.

When $R^2$ represents an alkoxyl group, the sum total of the carbon atom number is from 14 to 40, more preferably from 18 to 35. The alkoxyl group may further be substituted, and those described as substituents which may be substituted when R represents an alkyl group or an aryl group can be cited as substituents of the alkoxyl group.

Examples of alkoxyl groups include stearyloxy, myristyloxy, eicosyloxy and the structural formula shown below:

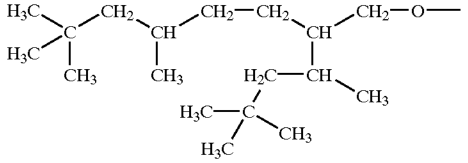

When $R^2$ represents —$NR^3R^4$ ($R^3$ and $R^4$ each independently represents an alkyl group having from 1 to 40 carbon atoms, a hydrogen atom, or an aryl group), the —$NR^3R^4$ group has the sum total of from 14 to 40 carbon atoms, more preferably from 18 to 35. Specific examples of —$NR^3R^4$ include distearylamino, dimyristylamino, dioctylamino, di(2-ethylhexyl)amino, stearylamino, lauryloxypropylamino, and anilino.

When $R^2$ represents a bicycloalkenyl group or a bicycloalkyl group, the sum total of the carbon atom number is from 14 to 40, preferably from 18 to 35. The bicycloalkenyl group or bicycloalkyl group preferably has [2,2,1] or [2,2,2]-bicyclo structure. Specific examples thereof include the following:

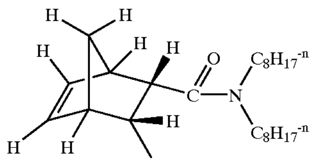

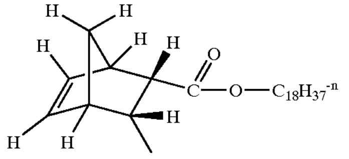

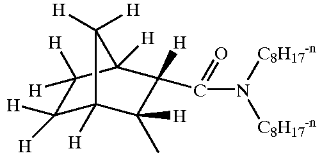

When $R^2$ represents a cycloalkenyl group or a cycloalkyl group, the sum total of the carbon atom number is from 14 to 40, preferably from 18 to 35. Specific examples of cycloalkenyl groups include 2-octyloxy-4-cyclopenten-1-yl and 4-stearyloxycarbonyl-2-cyclohexen-1-yl, and specific examples of cycloalkyl groups include 2-undecyloxycyclopentyl and 4-octyloxycarbonylcyclohexyl.

When $R^2$ represents a heterocyclic group, the sum total of the carbon atom number is from 14 to 40, preferably from 18 to 35. Specific examples of heterocyclic groups include the following:

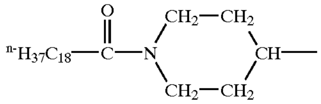

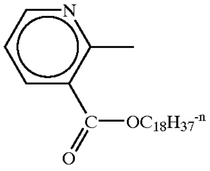

Of the above-described substituents, $R^2$ preferably represents a substituted or unsubstituted alkyl group having the sum total of from 14 to 40 carbon atoms, more preferably a substituted or unsubstituted alkyl group having the sum total of from 18 to 35 carbon atoms.

The compound represented by formula (I) preferably has the structure in which $R^2$ represents a substituted or unsubstituted alkyl group having the sum total of from 14 to 40 carbon atoms, $R^1$ represents an unsubstituted alkylene group having from 1 to 3 carbon atoms, and X is represented by formula (V).

Above all, the structure in which $R^2$ represents a substituted or unsubstituted alkyl group having the sum total of from 18 to 40 carbon atoms, $R^1$ represents a methylene group, and X represents —CO—OH is most preferred.

Specific examples of the compounds for use in the present invention are shown below, but the present invention is not limited thereto.

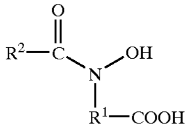

| Compound | $R^2$ | $R^1$ |
|---|---|---|
| 1 | $^{n}H_{31}C_{15}$— | —$CH_2$— |
| 2 | $^{n}H_{35}C_{17}$— | —$CH_2$— |
| 3 | $^{n}H_{39}C_{19}$— | —$CH_2$— |
| 4 | $^{n}H_{31}C_{15}$— | —$CH_2CH_2$— |
| 5 | $^{n}H_{35}C_{17}$— | —$CH_2CH_2CH_2$— |
| 6 | $^{n}H_{33}C_{16}$—O—$CH_2CH_2$— | 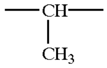 |
| 7 | $^{n}H_{37}C_{18}$—O—$CH_2$— | 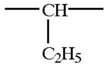 |
| 8 | $^{n}H_{29}C_{14}O$—$CH_2CH_2CH_2$— | —$CH_2CH_2$— |
| 9 | $(^{n}H_{17}C_8)_2$N—$CH_2CH_2$— | —$CH_2$— |
| 10 | $^{n}H_{37}C_{18}O$—$CH_2CH_2$— | —$CH_2$— |
| 11 | 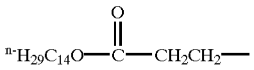 | —$CH_2$— |
| 12 | 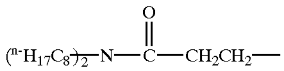 | —$CH_2CH_2CH_2$— |
| 13 | 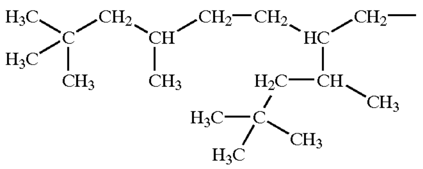 | —$CH_2$— |
| 14 | 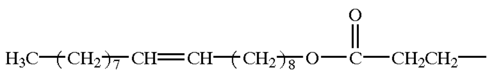 | —$CH_2$— |

-continued
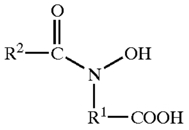
| Compound | $R^2$ | $R^1$ |
|---|---|---|
| 15 | 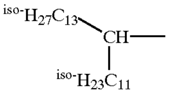 | $—CH_2CH_2CH_2CH_2CH_2—$ |
| 16 | 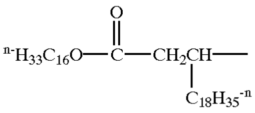 | $—CH_2CH_2—$ |
| 17 | 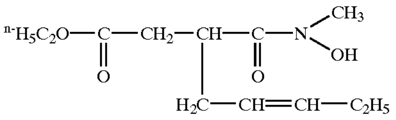 | $—CH_2—$ |
| 18 | 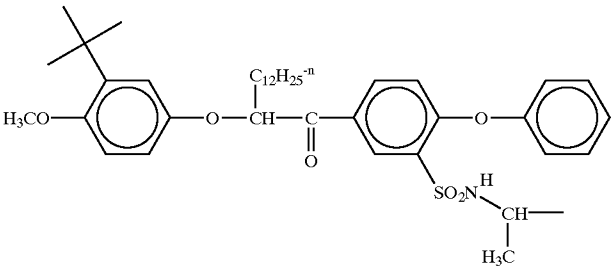 | $—CH_2—$ |
| 19 | 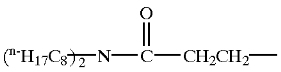 | $—CH_2CH_2CH_2—$ |
| 20 | 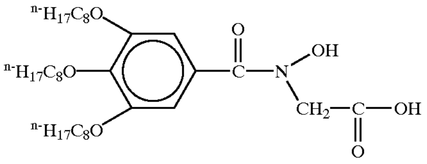 | |
| 21 | 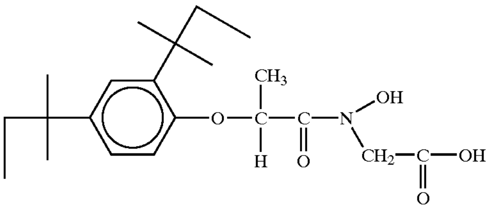 | |
| 22 | 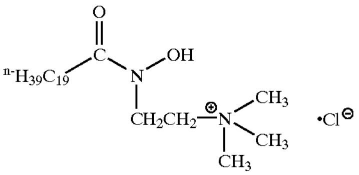 | |

-continued
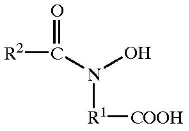
| Compound | $R^2$ | $R^1$ |
|---|---|---|
| 23 | 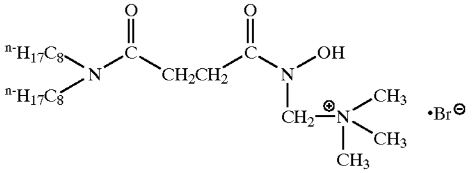 | |
| 24 | 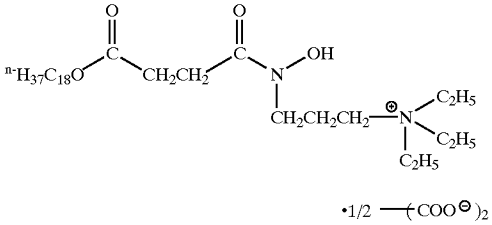 | |
| 25 | 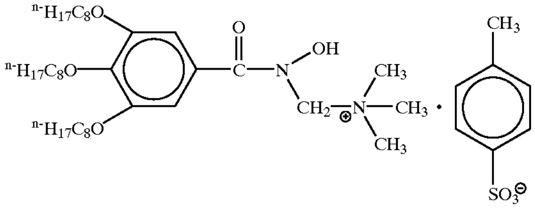 | |
| 26 | 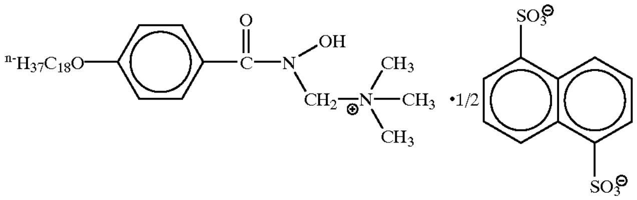 | |
| 27 | 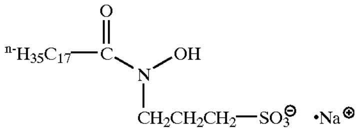 | |
| 28 | 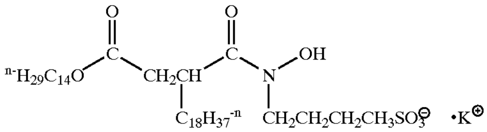 | |
| 29 | 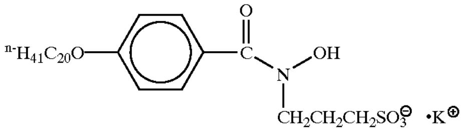 | |
| 30 | 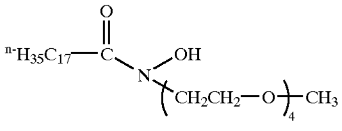 | |

-continued

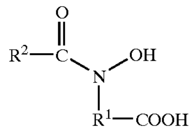

| Compound | $R^2$ | $R^1$ |
|---|---|---|
| 31 | 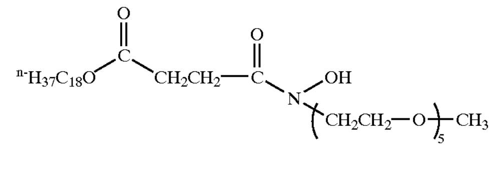 | |
| 32 | 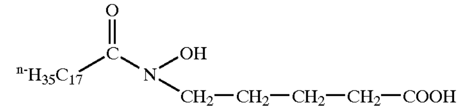 | |
| 33 | 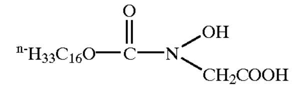 | |
| 34 | 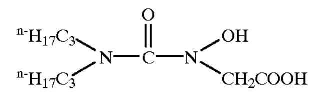 | |

General synthesis methods of the compounds of the present invention are shown below.

The compound of the present invention can be obtained by condensing the corresponding carboxylic acid chloride and a hydroxylamine. When the corresponding carboxylic acid is easily available, carboxylic acid chloride can easily be obtained by treating the carboxylic acid with thionyl chloride or oxalyl chloride. When the corresponding carboxylic acid is a complicated carboxylic acid, carboxylic acid chloride can be obtained by synthesizing the carboxylic acid according to a suitable synthesis method and treating the carboxylic acid with thionyl chloride or oxalyl chloride. Carboxylic acids can be synthesized according to the following synthesis methods.

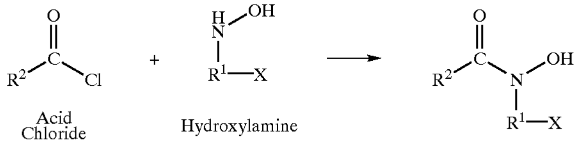

When X is represented by formula (III) or (IV), there is a case where the synthesis yield of acid chloride according to the above reaction scheme is low. In such a case, it is preferred to protect X with a protective group temporarily and release the protective group after the reaction of acid chloride and hydroxylamine.

The present invention is described by the synthesis examples of the compounds of the present invention.

SYNTHESIS EXAMPLE 1

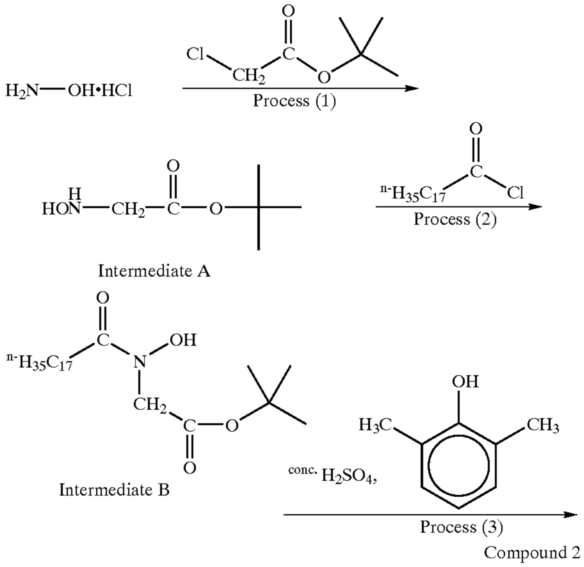

Process (1):

92.3 g of hydroxylamine hydrochloride, 111.7 g of sodium hydrogencarbonate, 200 ml of methanol and 110 g of t-butyl chloroacetate were reacted at 60° C. for 2 hours. The reaction solution was poured into water and extracted with ethyl acetate. The extracted product was dried with magnesium sulfate, the solvent was distilled off under reduced pressure and a coarse product was obtained. The obtained product was subjected to purification through a silica gel column chromatography to obtain 22.9 g of Intermediate A (yield: 22.7%).

Process (2):

While stirring 50 ml of water, 50 ml of ethyl acetate, 5.7 g of sodium hydrogencarbonate, and 5.0 g of Intermediate A under nitrogen atmosphere, 8.0 g of stearoyl chloride was dropwise added thereto at 10° C. Then, the temperature was raised to 40° C., the solution was separated, an organic phase was washed with water two times, dried over magnesium sulfate, then the solvent was distilled off under reduced pressure to obtain a coarse product. The obtained coarse product was recrystallized with a mixed solvent of hexane and acetonitrile to obtain 10.5 g of Intermediate B (yield: 96.3%).

Process 3:

9.2 g of Intermediate B, 2.6 g of 2,6-dimethylphenol, 90 ml of methylene chloride and 0.9 ml of a concentrated sulfuric acid were reacted at 20° C. for one day. Then, water and ethyl acetate were added thereto and the solution was separated at 50° C. An organic phase was washed with water two times, dried over magnesium sulfate, and the solvent was distilled off under reduced pressure.

The obtained crystal of Compound 2 was washed thoroughly with acetonitrile, dried, and 6.0 g of Compound 2 was obtained (yield: 78.1%).

300 MHz H NMR; $\delta D_2O$ (NaOD was added): 0.90 (3H, t), 1.20–1.46 (bs, 26H), 1.56 (bs, 2H), 2.22 (m, 1H), 2.48 (m, 1H), 3.28 (s, 1H), 4.11 (bs, 1H), 4.18 (s, 1H).

SYNTHESIS EXAMPLE 2 chloride were distilled off under reduced pressure with an aspirator to thereby obtain Intermediate C. Intermediate C was used in the next process as it was.

Process (2):

While stirring 50 ml of water, 50 ml of ethyl acetate, 5.7 g of sodium hydrogencarbonate, and 5.0 g of Intermediate A under nitrogen atmosphere, 30 ml of a solution of ethyl acetate containing Intermediate C (the entire amount synthesized in the previous process) was dropwise added thereto at 10° C.

The solution was separated at 40° C., an organic phase was washed with water two times, dried over magnesium sulfate, then the solvent was distilled off under reduced pressure and a coarse product was obtained. The obtained product was subjected to purification through a silica gel column chromatography (eluate: methanol/methylene chloride=1/10) to obtain 10.8 g of Intermediate D (yield: 56.7%).

Process (3):

10.8 g of Intermediate D, 100 ml of methylene chloride, 2.3 g of 2,6-dimethylphenol, and 1.0 ml of a concentrated sulfuric acid were reacted at 20° C. for 3 hours. Then, ethyl acetate and water were added thereto and the solution was separated. An organic phase was washed with water two times, dried over magnesium sulfate, and the solvent was distilled off under reduced pressure to obtain a coarse product. The obtained product was subjected to purification through a silica gel column chromatography to obtain 6.5 g of Compound 20 (yield: 65.9%).

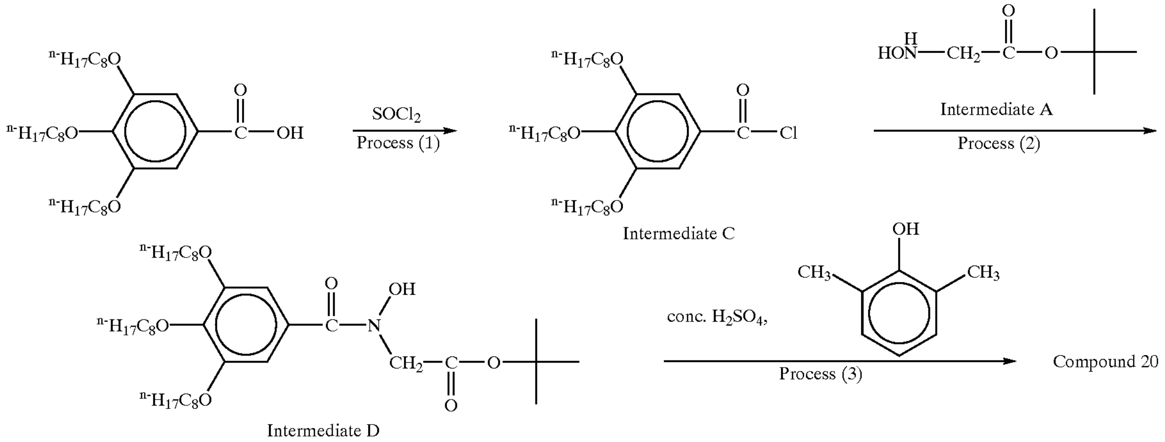

Process (1):

While stirring 15.2 g of 3,4,5-tri-n-octyloxybenzoic acid, 50 ml of methylene chloride and 0.5 ml of dimethylformamide, 4.3 g of thionyl chloride was dropwise added thereto. After the reaction was continued at 40° C. for 30 minutes, the remaining thionyl chloride and methylene 300 MHz H NMR; $\delta CDCl_3$: 0.89 (3H, t), 1.30 (8H, bs), 1.47 (2H, m), 1.78–1.88 (2H, m), 2.26 (2H, s), 4.20 (2H, t), 7.3 (1H, s).

SYNTHESIS EXAMPLE 3

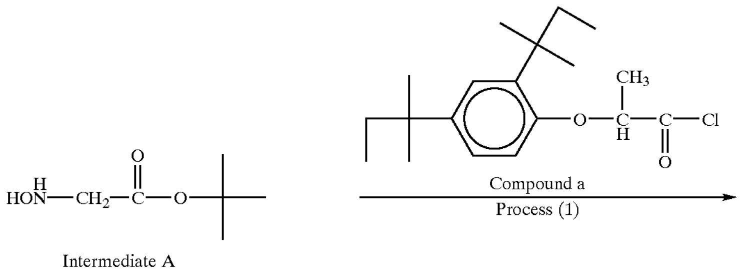

-continued

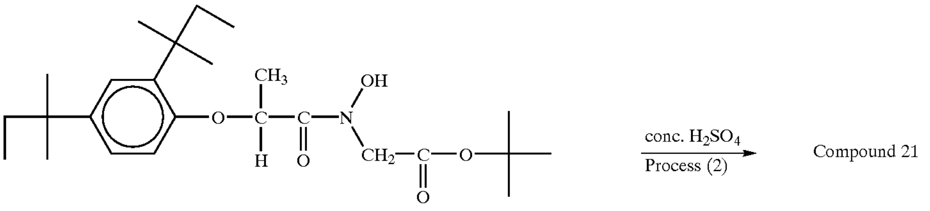

Intermediate E

Process (1):

While stirring 50 ml of water, 50 ml of ethyl acetate, 5.71 g of sodium hydrogencarbonate, and 5.0 g of Intermediate A under nitrogen atmosphere, 9.74 g of Compound a was dropwise added thereto at 10° C. The solution was separated at 40° C., an organic phase was washed with water two times, dried over magnesium sulfate, then the solvent was distilled off under reduced pressure and a coarse product was obtained. The obtained product was subjected to purification through a silica gel column chromatography to obtain 6.0 g of Intermediate E (yield: 40.5%).

Process (2):

4.0 g of Intermediate E, 40 ml of methylene chloride, and 0.4 ml of a concentrated sulfuric acid were mixed and reacted at 20° C. for 3 hours. Then, water and ethyl acetate were added thereto and the solution was separated. An organic phase was washed with water two times, dried over magnesium sulfate, then the solvent was distilled off under reduced pressure to obtain a coarse product. The obtained product was recrystallized with acetonitrile to obtain 3.1 g of Compound 21 (yield: 89.0%).

The structure was confirmed by 300 MHz $^1H$ NMR.

Other compounds of the present invention can also be synthesized in the same manner.

The compound represented by formula (I) preferably has a molecular weight of 280 or more, more preferably 300 or more, and most preferably 330 or more.

The compound of the present invention is necessary to be substantially insoluble in water in view of being non-diffusible in gelatin film. "Substantially insoluble in water" means the solubility in water at 25° C. is 10% or less, preferably 5% or less.

The raw material of the synthesis of the compound of the present invention (e.g., acid anhydrides and alcohols as described below) is sometimes available only as a mixture of an isomer and a homolog. Therefore, the compound of the present invention is sometimes easier to synthesize as a mixture of an isomer and a homolog. In such a case, the compound of the present invention is preferably added to a silver halide photographic material as a mixture.

The addition amount of the compound of the present invention is not particularly limited, but when the compound is added to a light-sensitive silver halide emulsion layer, the amount is preferably from $1.0 \times 10^{-5}$ to $1.0 \times 10^{-1}$ mol, more preferably from $1.0 \times 10^{-4}$ to $5.0 \times 10^{-2}$ mol, per mol of the silver in the same layer.

When the compound is added to a light-insensitive layer, the addition amount is preferably from $1 \times 10^{-6}$ to $3 \times 10^{-4}$ mol/m$^2$, more preferably from $1 \times 10^{-5}$ to $1 \times 10^{-4}$ mol/m$^2$.

The compound of the present invention may be added by dissolving in a water-soluble solvent (e.g., methanol, ethanol, acetone), may be added in the form of a co-emulsified dispersion with couplers and the like by an emulsified dispersion, or may be added previously at the time of the preparation of an emulsion, but the method of addition by an emulsified dispersion is most preferred.

There is no particular limitation on the layers to which the compound of the present invention is added but the compound is preferably added to a silver halide emulsion layer, and is more preferably added to a red-sensitive layer and/or a green-sensitive layer.

The present invention can be applied to various color photographic materials such as color negative films for general and cinematographic uses, color reversal films for slide and television uses, color papers, color positive films and color reversal papers. The present invention can also preferably be applied to the film units equipped with lenses as disclosed in JP-B-2-32615 (the term "JP-B" as used herein means an "examined Japanese patent publication") and JP-B-U-3-39784 (the term "JP-B-U" as used herein means an "examined Japanese utility model publication"). Further, the present invention can be applied to diffusion transfer color photographs using heat development, diffusion transfer photographs using autopositive emulsions, and wet type color reversal copying materials using autopositive emulsions. Moreover, the present invention can be applied to black-and-white photographic materials such as black-and-white negative films, microfilms, and X-ray films, but is preferably applied to general color and black-and-white photographic materials for photographing.

When the present invention is applied to a color photographic material, the material can comprise at least one light-sensitive layer on a support. In a typical embodiment, the silver halide photographic material of the present invention comprises at least one light-sensitive layer consisting of a plurality of silver halide emulsion layers having substantially the same spectral sensitivity but different degrees of sensitivity on a support. The light-sensitive layer is a unit light-sensitive layer having a spectral sensitivity to any of blue light, green light and red light. In the multilayer silver halide color photographic material, these unit light-sensitive layers are generally arranged in the order of red-sensitive layer, green-sensitive layer and blue-sensitive layer from the support side. However, the order of arrangement can be reversed depending on the purpose, alternatively, the light-sensitive layers may be arranged in such a way that a layer having a different spectral sensitivity is interposed between layers having the same spectral sensitivity as each other. Light-insensitive layers may be provided between the above-described silver halide light-sensitive layers, and on the uppermost layer and beneath the lowermost layer of the silver halide light-sensitive layers. These light-insensitive layers may contain couplers, DIR compounds and color mixing preventives described below. Further, these light-insensitive layers may contain compounds having a character of releasing a dye imagewise or inversely imagewise and making a difference in diffusibility between the released dye and the compound before release.

As the plurality of silver halide emulsion layers constituting each unit light-sensitive layer, a two-layer structure of a high sensitivity emulsion layer and a low sensitivity emulsion layer can be preferably used with the emulsion layers being arranged so as to decrease in sensitivity toward a support in turn as disclosed in German Patent 1,121,470 and British Patent 923,045. In addition, a low sensitivity emulsion layer may be provided farther from the support and a high sensitivity emulsion layer may be provided nearer to the support as disclosed in JP-A-57-112751, JP-A-62-200350, JP-A-62-206541 and JP-A-62-206543.

In one specific example, a low sensitivity blue-sensitive layer (BL)/a high sensitivity blue-sensitive layer (BH)/a high sensitivity green-sensitive layer (GH)/a low sensitivity green-sensitive layer (GL)/a high sensitivity red-sensitive layer (RH)/a low sensitivity red-sensitive layer (RL), or BH/BL/GL/GH/RH/RL, or BH/BL/GH/GL/RL/RH can be arranged in this order from the side farthest from the support.

A blue-sensitive layer/GH/RH/GL/RL can be arranged in this order from the side farthest from the support as disclosed in JP-B-55-34932. Further, a blue-sensitive layer/GL/RL/GH/RH can be arranged in this order from the side farthest from the support as disclosed in JP-A-56-25738 and JP-A-62-63936.

Further, useful arrangements include the arrangement in which there are three layers having different degrees of sensitivities with the sensitivity being lower towards the support such that the uppermost layer is a silver halide emulsion layer having the highest sensitivity, the middle layer is a silver halide emulsion layer having a lower sensitivity than that of the uppermost layer, and the lowermost layer is a silver halide emulsion layer having a lower sensitivity than that of the middle layer, as disclosed in JP-B-49-15495. In the case of the structure of this type comprising three layers having different degrees of sensitivity, the layers in the unit layer of the same spectral sensitivity may be arranged in the order of a middle sensitivity emulsion layer/a high sensitivity emulsion layer/a low sensitivity emulsion layer, from the side farthest from the support, as disclosed in JP-A-59-202464.

Alternatively, the layers can be arranged in the order of a high sensitivity emulsion layer/a low sensitivity emulsion layer/a middle sensitivity emulsion layer, or a low sensitivity emulsion layer/a middle sensitivity emulsion layer/a high sensitivity emulsion layer.

Moreover, the arrangement may be varied as indicated above in the case where there are four or more layers.

For improving color reproducibility, a donor layer (CL) for an interlayer effect having a different spectral sensitivity distribution from a main light-sensitive layer such as BL, GL and RL may preferably be provided adjacent or close to the main light-sensitive layer, as disclosed in U.S. Pat. Nos. 4,663,271, 4,705,744, 4,707,436, JP-A-62-160448 and JP-A-63-89850.

The silver halides preferably used in the present invention are silver iodobromide, silver iodochloride, silver iodochlorobromide, silver chlorobromide or silver chloride.

Silver halide grains in a photographic emulsion may have a regular crystal form such as a cubic, octahedral or tetradecahedral form, an irregular crystal form such as a spherical or plate-like form, a form which has crystal defects such as twinned crystal planes, or a form which is a composite of these forms.

The silver halide grains may be a fine grain having a grain size of about 0.2 μm or less, or large size grains having a projected area diameter of up to about 10 μm, and the emulsion may be a polydisperse emulsion or a monodisperse emulsion.

The silver halide photographic emulsions for use in the present invention can be prepared using the methods disclosed, for example, in *Research Disclosure* (hereinafter abbreviated to *RD*), No. 17643 (December, 1978), pages 22 and 23, "I. Emulsion Preparation and Types", *RD*, No. 18716 (November, 1979), page 648, *RD*, No. 307105 (November, 1989), pages 863 to 865, P. Glafkides, *Chimie et Physique Photographique*, Paul Montel (1967), G. F. Duffin, *Photographic Emulsion Chemistry*, Focal Press (1966), and V. L. Zelikman et al., *Making and Coating Photographic Emulsion*, Focal Press (1964).

The monodisperse emulsions disclosed in U.S. Pat. Nos. 3,574,628, 3,655,394 and British Patent 1,413,748 are also preferred.

Further, tabular grains having an aspect ratio of about 3 or more can also be used in the present invention. Tabular grains can be easily prepared according to the methods disclosed, for example, in Gutoff, *Photographic Science and Engineering*, Vol. 14, pages 248 to 257 (1970), U.S. Pat. Nos. 4,434,226, 4,414,310, 4,433,048, 4,439,520 and British Patent 2,112,157.

The crystal structure may be uniform, or the interior and exterior parts of the grains may be comprised of different halogen compositions, or the grains may have a layered structure. Silver halides which have different compositions may be joined with an epitaxial junction or may be joined with compounds other than a silver halide, such as silver thiocyanate or lead oxide. Further, mixtures of grains which have various crystal forms may also be used.

The above described emulsions may be of the surface latent image type wherein the latent image is primarily formed on the surface, or of the internal latent image type wherein the latent image is formed within the grains, or of a type wherein the latent image is formed both at the surface and within the grains. These emulsions may be a negative type emulsion or a positive type emulsion (a so-called autopositive emulsion). Further, a negative type emulsion may be a general negative type emulsion or may be a heat-developable negative type emulsion. Of the internal latent image types, the emulsion may be a core/shell type internal latent image type emulsion as disclosed in JP-A-63-264740, and a method for preparation of such a core/shell type internal latent image type emulsion is disclosed in JP-A-59-133542. The thickness of the shell of this emulsion varies depending on the development process, but is preferably from 3 to 40 nm, and particularly preferably from 5 to 20 nm.

The silver halide emulsion for use in the present invention is usually subjected to physical ripening, chemical ripening and spectral sensitization. Additives for use in such processes are disclosed in *RD*, No. 17643, *RD*, No. 18716, and *RD*, No. 307105, and the locations of these disclosures are summarized in a table below.

In the photographic material of the present invention, two or more different types of emulsions which are different in terms of at least one of the characteristics of grain size, grain size distribution, halogen composition, the form of the grains, or light sensitivity of the light-sensitive silver halide emulsion can be used in admixture in the same layer.

It is preferred to use the silver halide grains having a fogged grain surface as disclosed in U.S. Pat. No. 4,082,553, the silver halide grains having a fogged grain interior as disclosed in U.S. Pat. No. 4,626,498 and JP-A-59-214852, or colloidal silver in light-sensitive silver halide emulsion layers and/or substantially light-insensitive hydrophilic colloid layers. Silver halide grains having a fogged grain interior or surface are silver halide grains which can be developed uniformly (not imagewise) irrespective of whether these grains are in an unexposed part or an exposed part of the photographic material, and methods for the preparation thereof are disclosed in U.S. Pat. No. 4,626,498 and JP-A-59-214852. The silver halide which forms the internal nuclei of a core/shell type silver halide grains having a fogged grain interior may have different halogen compositions. The silver halide having a fogged grain interior or surface may be any of silver chloride, silver chlorobromide, silver iodobromide, or silver chloroiodobromide. The average grain size of these fogged silver halide grains is preferably from 0.01 to 0.75 μm, and particularly preferably from 0.05 to 0.6 μm. Further, the form of the grains may be regular grains and may be a polydisperse emulsion, but a monodisperse emulsion (at least 95% of which have a grain size within ±40% of the average grain size in terms of the weight or number of silver halide grains) is preferred.

The use of light-insensitive fine grained silver halides is preferred in the present invention. Light-insensitive fine grained silver halides are fine grained silver halides which are not sensitive to light upon imagewise exposure for obtaining color images and which do not substantially undergo development during development processing, and they are preferably not pre-fogged. The fine grained silver halide has a silver bromide content of from 0 to 100 mol %, and may contain silver chloride and/or silver iodide, if necessary. The fine grained silver halides which have a silver iodide content of from 0.5 to 10 mol % are preferred. The average grain size of the fine grained silver halide (the average value of the diameters of the circles corresponding to the projected areas) is preferably from 0.01 to 0.5 μm, more preferably from 0.02 to 0.2 μm.

The fine grained silver halide can be prepared by the same methods as the preparation of generally used light-sensitive silver halides. In the preparation of the fine grained silver halide, the surface of the silver halide grains does not need to be optically sensitized and also does not need to be spectrally sensitized. However, it is preferred to previously include known stabilizers such as triazole based, azaindene based, benzothiazolium based, or mercapto based compounds, or zinc compounds in the fine grained silver halide before addition to the coating solution. Colloidal silver can be included in the layer containing the fine grained silver halide grains.

The coating weight of silver in the photographic material of the present invention is preferably 6.0 $g/m^2$ or less, and most preferably 4.5 $g/m^2$ or less.

Photographic additives which can be used in the present invention are disclosed in *RD* and the locations related thereto are indicated in the table below.

Various dye-forming couplers can be used in the present invention, and the following couplers are particularly preferred.

Yellow Couplers:

The couplers represented by formula (I) or (II) disclosed in EP-A-502424; the couplers represented by formula (1) or (2) disclosed in EP-A-513496 (in particular, Y-28 on page 18); the couplers represented by formula (I) disclosed in claim 1 of JP-A-5-307248; the couplers represented by formula (I), lines 45 to 55, column 1 of U.S. Pat. No. 5,066,576; the couplers represented by formula (I), paragraph 0008 of JP-A-4-274425; the couplers disclosed in claim 1 on page 40 of EP-A-498381 (in particular, D-35 on page 18); the couplers represented by formula (Y) on page 4 of EP-A-447969 (in particular, Y-1 (page 17) and Y-54 (page 41)); and the couplers represented by any of formulae (II) to (IV), lines 36 to 58, column 7 of U.S. Pat. No. 4,476,219 (in particular, II-17 and II-19 (column 17), and II-24 (column 19)).

Magenta Couplers:

L-57 (page 11, right lower column), L-68 (page 12, right lower column), and L-77 (page 13, right lower column) of JP-A-3-39737; A-4-63 (page 134), and A-4-73 to A-4-75 (page 139) of European Patent 456257; M-4 to M-6 (page 26) and M-7 (page 27) of European Patent 486965; M-45, paragraph 0024 of JP-A-6-43611; M-1, paragraph 0036 of JP-A-5-204106; and M-22, paragraph 0237 of JP-A-4-362631.

Cyan Couplers:

CX-1, CX-3, CX-4, CX-5, CX-11, CX-12, CX-14 and CX-15 (pages 14 to 16) of JP-A-4-204843; C-7 and C-10 (page 35), C-34 and C-35 (page 37), and (I-1) and (I-17) (pages 42 and 43) of JP-A-4-43345; and the couplers represented by formula (Ia) or (Ib) disclosed in claim 1 of JP-A-6-67385.

Polymer Couplers:

P-1 and P-5 (page 11) of JP-A-2-44345.

Couplers the Colored Dyes of Which Have an Appropriate Diffusibility:

The couplers disclosed in U.S. Pat. No. 4,366,237, British Patent 2,125,570, EP-B-96873 and German Patent 3,234,533 are preferred as couplers the colored dyes of which have an appropriate diffusibility.

Couplers for Correcting the Unnecessary Absorption of Colored Dyes:

Examples of preferred couplers for correcting the unnecessary absorption of colored dyes include the yellow colored cyan couplers represented by formula (CI), (CII), (CIII) or (CIV) disclosed on page 5 of EP-A-456257 (in particular,

| Type of Additives | RD 17643 | RD 18716 | RD 307105 |
|---|---|---|---|
| 1. Chemical Sensitizers | page 23 | page 648, right column | page 866 |
| 2. Sensitivity Increasing Agents | — | page 648, right column | — |
| 3. Spectral Sensitizers and Supersensitizers | pages 23–24 | page 648, right column to page 649, right column | pages 866–868 |
| 4. Whitening Agents | page 24 | page 647, right column | page 868 |
| 5. Light Absorbers, Filter Dyes, and Ultraviolet Absorbers | pages 25–26 | page 649, right column to page 650, left column | page 873 |
| 6. Binders | page 26 | page 651, left column | pages 873–874 |
| 7. Plasticizers and Lubricants | page 27 | page 650, right column | page 876 |
| 8. Coating Aids and Surfactants | pages 26–27 | page 650, right column | pages 875–876 |
| 9. Antistatic Aqents | page 27 | page 650, right column | pages 876–877 |
| 10. Matting Agents | — | — | pages 878–879 |

YC-86 on page 84); the yellow colored magenta couplers ExM-7 (page 202), EX-1 (page 249), and EX-7 (page 251) disclosed in EP-A-456257; the magenta colored cyan couplers CC-9 (column 8) and CC-13 (column 10) disclosed in U.S. Pat. No. 4,833,069; the coupler (2) (column 8) of U.S. Pat. No. 4,837,136; and the colorless masking couplers represented by formula (A) disclosed in claim 1 of WO 92/11575 (in particular, the compounds disclosed on pages 36 to 45).

Examples of compounds (inclusive of couplers) which release photographically useful residual groups of compounds upon reacting with the oxidation product of a developing agent include the following:

Development Inhibitor Releasing Compounds:

The compounds represented by formula (I), (II), (III) or (IV) disclosed on page 11 of EP-A-378236 (in particular, T-101 (page 30), T-104 (page 31), T-113 (page 36), T-131 (page 45), T-144 (page 51) and T-158 (page 58)); the compounds represented by formula (I) disclosed on page 7 of EP-A-436938 (in particular, D-49 (page 51)); the compounds represented by formula (I) disclosed in JP-A-5-307248 (in particular, (23), paragraph 0027); and the compounds represented by formula (I), (II) or (III) disclosed on pages 5 and 6 of EP-A-440195 (in particular, I-(1) on page 29);

Bleaching Accelerator Releasing Compounds:

The compounds represented by formula (I) or (I') disclosed on page 5 of EP-A-310125 (in particular, (60) and (61) on page 61); and the compounds represented by formula (I) disclosed in claim 1 of JP-A-6-59411 (in particular, (7), paragraph 0022);

Ligand Releasing Compounds:

The compounds represented by LIG-X disclosed in claim 1 of U.S. Pat. No. 4,555,478 (in particular, the compounds in lines 21 to 41, column 12);

Leuco Dye Releasing Compounds:

Compounds 1 to 6, columns 3 to 8 of U.S. Pat. No. 4,749,641.

Fluorescent Dye Releasing Compounds:

The compounds represented by COUP-DYE disclosed in claim 1 of U.S. Pat. No. 4,774,181 (in particular, compounds 1 to 11, columns 7 to 10);

Development Accelerator Releasing or Fogging Agent Releasing Compounds:

The compounds represented by formula (1), (2) or (3), column 3 of U.S. Pat. No. 4,656,123 (in particular, (I-22), column 25); and compound ExZK-2, lines 36 to 38, page 75 of EP-A-450637; and Compounds Which Release Dyes the Color of Which Is Restored after Elimination:

The compounds represented by formula (I) disclosed in claim 1 of U.S. Pat. No. 4,857,447 (in particular, Y-1 to Y-19, columns 25 to 36).

Preferred additives other than couplers are listed below:

Dispersion Mediums of Oil-Soluble Organic Compound:

P-3, P-5, P-16, P-19, P-25, P-30, P-42, P-49, P-54, P-55, P-66, P-81, P-85, P-86 and P-93 (pages 140 to 144) of JP-A-62-215272;

Latexes for Impregnation of Oil-Soluble Organic Compound:

The latexes disclosed in U.S. Pat. No. 4,199,363;

Scavengers for the Oxidation Product of a Developing Agent:

The compounds represented by formula (I), lines 54 to 62, column 2 of U.S. Pat. No. 4,978,606 (in particular, I-(1), I-(2), I-(6) and I-(12), columns 4 and 5), and the compounds represented by the formula disclosed in lines 5 to 10, column 2 of U.S. Pat. No. 4,923,787 (in particular, compound 1, column 3);

Stain Inhibitors:

The compounds represented by formula (I), (II) or (III), lines 30 to 33, page 4 of EP-A-298321 (in particular, I-47, I-72, III-1 and III-27, pages 24 to 48);

Discoloration Inhibitors:

A-6, A-7, A-20, A-21, A-23, A-24, A-25, A-26, A-30, A-37, A-40, A-42, A-48, A-63, A-90, A-92, A-94 and A-164 (pages 69 to 118) of EP-A-298321; II-1 to III-23, columns 25 to 38 of U.S. Pat. No. 5,122,444 (in particular, III-10); I-1 to III-4, pages 8 to 12 of EP-A-471347 (in particular, II-2); and A-1 to A-48, columns 32 to 40 of U.S. Pat. No. 5,139,931 (in particular, A-39 and A-42);

Compounds for Reducing the Using Amounts of Color Intensifiers and Color Mixing Preventives:

I-1 to II-15, pages 5 to 24 of EP-A-411324 (in particular, I-46);

Formaldehyde Scavengers:

SCV-1 to SCV-28, pages 24 to 29 of EP-A-477932 (in particular, SCV-8);

Hardening Agents:

H-1, H-4, H-6, H-8 and H-14 on page 17 of JP-A-1-214845; the compounds represented by any of formulae (VII) to (XII), columns 13 to 23 of U.S. Pat. No. 4,618,573 (H-1 to H-54); the compounds represented by formula (6), right lower column, page 8 of JP-A-2-214852 (H-1 to H-76) (in particular, H-14), and the compounds disclosed in claim i of U.S. Pat. No. 3,325,287;

Development Inhibitor Precursors:

P-24, P-37 and P-39, pages 6 and 7 of JP-A-62-169139; and the compounds disclosed in claim 1 of U.S. Pat. No. 5,019,492 (in particular, compounds 28 and 29, column 7);

Fungicides and Biocides:

I-1 to III-43, columns 3 to 15 of U.S. Pat. No. 4,923,790 (in particular, II-1, II-9, II-10, II-18 and III-25);

Stabilizers and Antifoggants:

I-1 to (14), columns 6 to 16 of U.S. Pat. No. 4,923,793 (in particular, I-1, 60, (2) and (13)); and compounds 1 to 65, columns 25 to 32 of U.S. Pat. No. 4,952,483 (in particular, compound 36);

Chemical Sensitizers:

Triphenylphosphine selenide; and compound 50 disclosed in JP-A-5-40324;

Dyes:

a-1 to b-20, pages 15 to 18 (in particular, a-1, a-12, a-18, a-27, a-35, a-36, and b-5), and V-1 to V-23, pages 27 to 29 (in particular, V-1) of JP-A-3-156450; F-I-1 to F-II-43, pages 33 to 55 of EP-A-445627 (in particular, F-I-11 and F-II-8); III-1 to III-36, pages 17 to 28 of EP-A-457153 (in particular, III-1 and III-3); crystallite dispersions of Dye-1 to Dye-124, pages 8 to 26 of WO 88/04794; compounds 1 to 22, pages 6 to 11 of EP-A-319999 (in particular, compound 1); compounds D-1 to D-87 represented by any of formulae (1) to (3), pages 3 to 28 of EP-A-519306; compounds 1 to 22 represented by formula (I), columns 3 to 10 of U.S. Pat. No. 4,268,622; and compounds (1) to (31) represented by formula (I), columns 2 to 9 of U.S. Pat. No. 4,923,788;

Ultraviolet Absorbers:

Compounds (18b) to (18r) represented by formula (1), 101 to 427, pages 6 to 9 of JP-A-46-3335; compounds (3) to (66) represented by formula (I), pages 10 to 44, and compounds HBT-1 to HBT-10 represented by formula (III), page 14, of EP-A-520938; and compounds (1) to (31) represented by formula (1), columns 2 to 9 of EP-A-521823.

Suitable supports which can be used in the present invention are disclosed, for example, in *RD*, No. 17643, page 28, *RD*, No. 18716, from right column, page 647 to left column, page 648, and *RD*, No. 307105, page 879.

The photographic material of the present invention has a total film thickness of all the hydrophilic colloid layers on the side where the silver halide emulsion layers are located of preferably 28 μm or less, more preferably 23 μm or less, still more preferably 18 μm or less, and most preferably 16 μm or less. Further, the film swelling rate $T_{1/2}$ is preferably 30 seconds or less, more preferably 20 seconds or less. $T_{1/2}$ is defined as the time to reach ½ of the saturated film thickness, taking 90% of the maximum swollen film thickness reached when being processed at 30° C. for 3 minutes and 15 seconds in a color developing solution as the saturated film thickness. The film thickness means the film thickness measured under conditions of 25° C., 55% relative humidity (stored for 2 days), and $T_{1/2}$ can be measured using a swellometer of the type described in A. Green, *Photogr. Sci. Eng.*, Vol. 19, No. 2, pages 124 to 129. $T_{1/2}$ can be adjusted by adding hardening agents to gelatin which is used as a binder, or by changing the aging conditions after coating. Further, a swelling factor of from 150% to 400% is preferred. The swelling factor can be calculated from the maximum swollen film thickness obtained under the conditions described above using the equation: (maximum swollen film thickness–film thickness)/film thickness.

The provision of hydrophilic colloid layers (known as backing layers) having a total dry film thickness of from 2 μm to 20 μm on the side of the support opposite to the side on which emulsion layers are provided is preferred in the photographic material of the present invention. The inclusion of the above described light absorbers, filter dyes, ultraviolet absorbers, antistatic agents, hardening agents, binders, plasticizers, lubricants, coating aids, and surfactants in the backing layers is preferred. The swelling factor of the backing layer is preferably from 150 to 500%.

The photographic material of the present invention can be development processed by the ordinary methods disclosed in *RD*, No. 17643, pages 28 and 29, *RD*, No. 18716, from left column to right column, page 651, and *RD*, No. 307105, pages 880 and 881.

The color developing solution for use in the development processing of the photographic material of the present invention is preferably an alkaline aqueous solution which contains an aromatic primary amine color developing agent as a main component. Aminophenol based compounds are useful as a color developing agent, but the use of p-phenylenediamine based compounds is preferred, and representative examples thereof include the compounds disclosed in lines 43 to 52, page 28 of EP-A-556700. Two or more of these compounds can be used in combination according to purposes.

The color developing solution generally contains a pH buffer such as alkali metal carbonate, borate orphosphate, or a development inhibitor or an antifoggant such as chloride, bromide, iodide, benzimidazoles, benzothiazoles, or mercapto compounds. The color developing solution may also contain, if necessary, various preservatives such as hydroxylamine, diethylhydroxylamine, sulfite, hydrazines, e.g., N,N-bis-carboxymethylhydrazine, phenylsemicarbazides, triethanolamine and catecholsulfonic acids, an organic solvent such as ethylene glycol and diethylene glycol, a development accelerator such as benzyl alcohol, polyethylene glycol, quaternary ammonium salt, and amines, a dye-forming coupler, a competitive coupler, an auxiliary developing agent such as 1-phenyl-3-pyrazolidone, a thickener, and various chelating agents typified by aminopolycarboxylic acid, aminopolyphosphonic acid, alkylphosphonic acid, and phosphonocarboxylic acid, e.g., ethylenediaminetetraacetic acid, nitrilotriacetic acid, diethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N,N-tetramethylenephosphonic acid, ethylenediamine-di(o-hydroxyphenylacetic acid) and salts of these acids.

Further, the color development is generally carried out after the black-and-white development in the case of reversal processing. In the black-and-white developing solution, known black-and-white developing agents such as dihydroxybenzenes, e.g., hydroquinone, 3-pyrazolidones, e.g., 1-phenyl-3-pyrazolidone, or aminophenols, e.g., N-methyl-p-aminophenol can be used alone or in combination. The pH of these color developing solution and black-and-white developing solution is generally from 9 to 12. The replenishment rate of these developing solutions depends on the color photographic material to be processed but, in general, it is 3 liters or less per square meter of the photographic material, and the amount can be reduced to 500 ml or less by reducing the bromide ion concentration in the replenisher. In the case when the replenishment rate is reduced, it is preferred to prevent evaporation and air oxidation of the solution by minimizing the area of contact of the solution with the air in the processing tank.

The processing effect by the contact of the photographic processing solution with the air in a processing tank can be evaluated by the following equation: Open factor ($cm^{-1}$)=[Contact area of processing solution with air ($cm^{-2}$)]÷[Volume of processing solution ($cm^{-3}$)]. This open factor is preferably 0.1 ($cm^{-1}$) or less, more preferably from 0.001 to 0.05 ($cm^{-1}$). The method using a movable lid as disclosed in JP-A-1-82033 and the slit development processing method as disclosed in JP-A-63-216050 can be used as means of reducing the open factor, as well as the provision of a shielding material such as a floating lid on the surface of the photographic processing solution in the processing tank. Reduction of the open factor is preferred not only in the processes of the color development and the black-and-white development but also in all the subsequent processes such as the bleaching process, the bleach-fixing process, the fixing process, the washing process and the stabilizing process. Further, the replenishment rate can be reduced by suppressing the accumulation of the bromide ion in the developing solution.

The color development processing time is usually set between 2 and 5 minutes, but shorter processing time is available by raising the temperature and the pH and increasing the concentration of the color developing agent.

A photographic emulsion layer is generally bleaching processed after being color development processed. A bleaching process and a fixing process may be carried out at the same time (bleach-fixing process) or may be performed separately. A processing method comprising carrying out a bleach-fixing process after a bleaching process can be adopted for further rapid processing. Also, processing in two successive bleach-fixing baths, fixing process before bleach-fixing process, or bleaching process after bleach-fixing process may optionally be selected according to purposes. Compounds of polyvalent metals such as iron(III), peracids, quinones, and nitro compounds are used as a bleaching agent. Representative examples of bleaching agents which are preferably used in the present invention include a complex salt such as organic complex salts of iron(III) with aminopolycarboxylic acids, e.g., ethylenediaminetetraacetic acid, diethylenetriaminepentaacetic acid, cyclohexanediaminetetraacetic acid, methyliminodiacetic acid, 1,3-diaminopropanetetraacetic acid, and glycol ether diaminetetraacetic acid, or citric acid, tartaric acid or malic acid. The use of aminopolycarboxylic acid iron(III) complex salts such as ethylenediaminetetraacetic acid iron(III) complex salts and 1,3-diaminopropanetetraacetic acid iron(III) complex salts is particularly preferred of them from the point of providing rapid processing and preventing environmental pollution. Further, aminopolycarboxylic acid iron(III) complex salts are particularly useful in both of a bleaching solution and a bleach-fixing solution. The pH of the bleaching solution or the bleach-fixing solution in which these aminopolycarboxylic acid iron(III) complex salts are included is generally from 4.0 to 8, but lower pH can be used to speed up the processing.

Bleaching accelerators can be used, if necessary, in the bleaching solution, the bleach-fixing solution, or the prebaths thereof. Specific examples of useful bleaching accelerators are disclosed in the following publications: the compounds which have a mercapto group or a disulfido group disclosed in U.S. Pat. No. 3,893,858, German Patents 1,290,812, 2,059,988, JP-A-53-32736, JP-A-53-57831, JP-A-53-37418, JP-A-53-72623, JP-A-53-95630, JP-A-53-95631, JP-A-53-104232, JP-A-53-124424, JP-A-53-141623, JP-A-53-28426, and *RD*, No. 17129 (July, 1978); the thiazolidine derivatives disclosed in JP-A-50-140129; the thiourea derivatives disclosed in JP-B-45-8506, JP-A-52-20832, JP-A-53-32735, and U.S. Pat. No. 3,706,561; the iodides disclosed in German Patent 1,127,715 and JP-A-58-16235; the polyoxyethylene compounds disclosed in German Patents 966,410 and 2,748,430; the polyamine compounds disclosed in JP-B-45-8836; the other compounds disclosed in JP-A-49-40943, JP-A-49-59644, JP-A-53-94927, JP-A-54-35727, JP-A-55-26506 and JP-A-58-163940; and bromide ions. The compounds which have a mercapto group or a disulfido group are preferred from the point of providing large accelerating effect, and those disclosed in U.S. Pat. No. 3,893,858, German Patent 1,290,812 and JP-A-53-95630 are particularly preferred of all. Further, the compounds disclosed in U.S. Pat. No. 4,552,834 are also preferred. These bleaching accelerators can be included in photographic materials. These bleaching accelerators are especially effective when bleach-fixing color photographic materials for photographing.

It is preferred to include organic acids in a bleaching solution and a bleach-fixing solution, in addition to the above compounds, for inhibiting bleaching stain. Particularly preferred organic acids are compounds having an acid dissociation constant (pKa) of from 2 to 5, specifically, acetic acid, propionic acid, and hydroxyacetic acid are preferred.

Thiosulfate, thiocyanate, thioether based compounds, thioureas, and a large amount of iodide can be used as the fixing agent which is used in a fixing solution and a bleach-fixing solution, but thiosulfate is generally used, in particular, ammonium thiosulfate can be most widely used. Further, the combined use of thiosulfate with thiocyanate, thioether based compounds and/or thiourea is also preferred. As preservatives for a fixing solution and a bleach-fixing solution, sulfite, bisulfite, carbonyl-bisulfite addition products or the sulfinic acid compounds disclosed in EP-A-294769 are preferred. Moreover, aminopolycarboxylic acids and organic phosphonic acids are preferably added to a fixing solution and a bleach-fixing solution for stabilizing the solutions.

In the present invention, compounds having a pKa of from 6.0 to 9.0 are preferably added to a fixing solution or a bleach-fixing solution for controlling pH, preferably imidazoles such as imidazole, 1-methylimidazole, 1-ethylimidazole and 2-methylimidazole, in an amount of from 0.1 to 10 mol per liter.

The total processing time of the desilvering process is preferably shorter in the range not generating a desilvering failure. The desilvering processing time is preferably from 1 minute to 3 minutes and more preferably from 1 minute to 2 minutes. Further, the processing temperature is generally from 25° C. to 50° C., and preferably from 35° C. to 45° C. In the preferred temperature range, the desilvering rate is increased and the occurrence of staining after processing is effectively prevented.

Stirring as vigorous as possible in the desilvering process is preferred. Specific examples of the methods of forced stirring include the method wherein a jet of the processing solution is impinged on the surface of the emulsion of the photographic material as disclosed in JP-A-62-183460, the method wherein the stirring effect is raised using a rotating means as disclosed in JP-A-62-183461, the method wherein the photographic material is moved with a wiper blade, which is installed in the solution, in contact with the surface of the emulsion, and the generated turbulent flow at the surface of the emulsion increases the stirring effect, and the method wherein the circulating flow rate of the entire processing solution is increased. These means for increasing the stirring level are effective for the bleaching solution, the bleach-fixing solution and the fixing solution. It is supposed that the increased stirring level increases the rate of supply of the bleaching agent and the fixing agent to the emulsion film and, as a result, increases the desilvering rate. Further, the above means of increasing stirring are more effective when a bleaching accelerator is used, and it is possible to extremely increase the bleaching accelerating effect and to eliminate the fixing hindrance action due to the bleaching accelerator.

The automatic processors which are used in the present invention preferably have the means of transporting photographic materials as disclosed in JP-A-60-i91257, JP-A-60-191258, and JP-A-60-191259. As described in the above JP-A-60-191257, such a transporting means can greatly reduce the carryover of the processing solution from the previous bath to the next bath and effectively prevent the deterioration of the capabilities of the processing solution, and is especially effective in reducing the processing time of each processing step and reducing the replenishment rate of each processing solution.

The photographic material of the present invention is generally subjected to a washing step and/or a stabilizing step after the desilvering step. The amount of washing water in the washing step can be selected from a wide range according to the characteristics and the application of the photographic materials (for example, the materials used such as couplers, etc.), the temperature of a washing water, the number of washing tanks (the number of washing stages), the replenishing system, that is, whether a countercurrent system or a concurrent system, and other various conditions. Of the foregoing conditions, the relationship between the number of washing tanks and he amount of water in a multistage countercurrent system can be obtained by the method described in *Journal of the Society of Motion Picture and Television Engineers*, Vol. 64, pages 248 to 253 (May, 1955). According to the multistage countercurrent system of the above literature, the amount of the washing water can be greatly reduced, however, problems arise that bacteria proliferate due to the increased residence time of the water in the tanks, and suspended matters produced thereby adhere to the photographic material. The method of reducing the calcium ion and magnesium ion concentrations as disclosed in JP-A-62-288838 can be used as a very effective means for overcoming these problems. Also, the isothiazolone compounds and the thiabendazoles as disclosed in JP-A-57-8542, the chlorine based antibacterial agents such as chlorinated sodium isocyanurate, the benzotriazoles, and the antibacterial agents disclosed in Hiroshi Horiguchi, *Bohkin Bohbai no Kagaku* (*Antibacterial and Antifungal Chemistry*), published by Sankyo Shuppan K. K. (1986), *Biseibutsu no Mekkin, Sakkin, Bohbai Gijutsu* (*Germicidal and Antifungal Techniques of Microorganisms*), edited by Eisei Gijutsukai, published by Kogyo Gijutsukai (1982), and *Bohkin Bohbai Zai Jiten* (*Antibacterial and Antifungal Agents Thesaurus*), edited by Nippon Bohkin Bohbai Gakkai (1986), can be used.

The pH of the washing water in the processing of the photographic material of the present invention is generally from 4 to 9 and preferably from 5 to 8. The temperature and the time of a washing step can be selected variously according to the characteristics and the end use purpose of the photographic material to be processed, but is generally from 15 to 45° C. for 20 seconds to 10 minutes, and preferably from 25 to 40° C. for 30 seconds to 5 minutes. Further, the photographic material of the present invention can be processed directly with a stabilizing solution without employing a washing step as described above. Any known methods as disclosed in JP-A-57-8543, JP-A-58-14834 and JP-A-60-220345 can be used in such a stabilizing process.

Further, there is also a case in which a stabilizing process is carried out following the above described washing process, and the stabilizing bath which contains a dye stabilizer and a surfactant which is used as a final bath for color photographic materials for photographing is one example of such a process. Aldehydes such as formaldehyde and glutaraldehyde, N-methylol compounds, hexamethylenetetramine and sulfite addition products of aldehyde can be used as a dye stabilizer.

Various chelating agents and fungicides can also be added to a stabilizing bath.

The overflow generated by the replenishment of the above described washing water and/or stabilizing solution can be reused in other steps such as a desilvering step, etc.

When the above each processing solution is concentrated due to evaporation by the processing using an automatic processor, etc., it is preferred to replenish an appropriate amount of water for the correction of concentration.

Color developing agents may be incorporated into a photographic material of the present invention to simplify and speed up the processing. Color developing agent precursors are preferred for the incorporation. For example, the indoaniline based compounds disclosed in U.S. Pat. No. 3,342,597, the Schiff's base type compounds disclosed in U.S. Pat. No. 3,342,599, *Research Disclosure*, Nos. 14850 and 15159, the aldol compounds disclosed in *RD*, No. 13924, the metal complex salts disclosed in U.S. Pat. No. 3,719,492 and the urethane based compounds disclosed in JP-A-53-135628 can be used for this purpose.

Various 1-phenyl-3-pyrazolidones may be included, if required, in the photographic material of the present invention to accelerate color development. Typical compounds are disclosed in JP-A-56-64339, JP-A-57-144547 and JP-A-58-115438.

The processing solutions used for the processing of the photographic material of the present invention are used at a temperature of from 10° C. to 50° C. The standard temperature is generally from 33° C. to 38° C., but higher temperatures can be used to accelerate the processing to shorten the processing time, on the contrary, lower temperature can be used to improve the picture quality and stabilize the processing solutions.

When the present invention is applied to black-and-white photographic materials, various additives and development processing methods used therefor are not particularly limited, and those disclosed in the following places of JP-A-2-68539, JP-A-5-11389 and JP-A-2-58041 can be preferably used.

| | | |
|---|---|---|
| 1. | Silver halide emulsion and the preparation method thereof | from 6 lines up from the bottom, right lower column, page 8 to line 12, right upper column, page 10 of JP-A-2-68539 |
| 2. | Chemical sensitization method | from line 13, right upper column, page 10 to line 16, left lower column, page 10 of JP-A-2-68539; selenium sensitization method disclosed in JP-A-5-11389 |
| 3. | Antifoggant and stabilizer | from line 17, left lower column, page 10 to line 7, left upper column, page 11 of JP-A-2-68539; from line 2, left lower column, page 3 to left lower column, page 4 of JP-A-2-68539 |
| 4. | Spectral sensitizing dye | from line 4, right lower column, page 4 to right lower column, page 8 of JP-A-2-68539; from line 8, left lower column, page 12 to line 19, right lower column, page 12 of JP-A-2-58041 |
| 5. | Surfactant and antistatic agent | from line 14, left upper column, page 11 to line 9, left upper column, page 12 of JP-A-2-68539; from line 14, left lower column, page 2 to line 12, left lower column, page 5 of JP-A-2-58041 |
| 6. | Matting agent, plasticizer and sliding agent | from line 10, left upper column, page 12 to line 10, right upper column, page 12 of JP-A-2-68539; from line 13, left lower column, page 5 to line 3, left lower column; page 10 of JP-A-2-58041 |
| 7. | Hydrophilic colloid | from line 11, right upper column, page 12 to line 16, left lower column, page 12 of JP-A-2-68539 |
| 8. | Hardening agent | from line 17, left lower column page 12 to line 6, right upper column, page 13 of JP-A-2-68539 |
| 9 | Development processing method | from line 14, left upper column, page 15, to line 13, left lower column, page 15 of JP-A-2-68539 |

In addition to the above, the present invention can be applied to diffusion transfer photographs, so-called instant photographs. Examples of diffusion transfer photographs are disclosed in JP-A-5-297544.

The present invention can also be applied to heat-developable photographic materials. Heat-developable photographic materials to which the present invention can be applied may be either black-and-white photographic materials or color photographic materials, for example, those disclosed in JP-A-60-162251, JP-A-64-13546, JP-A-1-161236, U.S. Pat. Nos. 4,474,867, 4,478,927, 4,507,380, 4,500,626, 4,483,914, 4,783,396, 4,740,445, JP-A-59-231539, and JP-A-60-2950 can be cited.

Further, the present invention can be applied to wet type color reversal copying materials using autopositive emulsions. With respect to this material, Sample No. 101 in Example 1 of JP-A-3-152530 and Sample No. 1 in JP-A-2-90145 can be referred to as examples.

The present invention will be illustrated in more detail with reference to examples below, but these are not to be construed as limiting the present invention.

EXAMPLE 1

A multilayer color photographic material was prepared as Sample No. 101 by coating each layer having the following composition on an undercoated cellulose triacetate film support.

Composition of Light-Sensitive Layer

The main components for use in each layer are classified as follows:

ExC: Cyan Coupler

ExM: Magenta Coupler

ExY: Yellow Coupler

ExS: Sensitizing Dye

UV: Ultraviolet Absorber

HBS: High Boiling Point Organic Solvent

H: Gelatin Hardening Agent

The numeral corresponding to each component indicates the coated weight in unit of g/m$^2$, and the coated weight of silver halide is shown in terms of silver. Further, the coated weight of a sensitizing dye is indicated in unit of mol per mol of the silver halide in the same layer.

| | |
|---|---|
| First Layer: Antihalation Layer | |
| Black Colloidal Silver | 0.09 as silver |
| Gelatin | 1.60 |
| ExM-1 | 0.12 |
| ExF-1 | $2.0 \times 10^{-3}$ |
| Solid Dispersion Dye ExF-2 | 0.030 |
| Solid Dispersion Dye ExF-3 | 0.040 |
| HBS-1 | 0.15 |
| HBS-2 | 0.02 |
| Second Layer: Interlayer | |
| Silver Iodobromide Emulsion M | 0.065 as silver |
| ExC-2 | 0.04 |
| Polyethyl Acrylate Latex | 0.20 |
| Gelatin | 1.04 |
| Third Layer: Low Sensitivity Red-Sensitive Emulsion Layer | |
| Silver Iodobromide Emulsion A | 0.25 as silver |
| Silver Iodobromide Emulsion B | 0.25 as silver |
| ExS-1 | $6.9 \times 10^{-5}$ |
| ExS-2 | $1.8 \times 10^{-5}$ |
| ExS-3 | $3.1 \times 10^{-4}$ |
| ExC-1 | 0.17 |
| ExC-3 | 0.030 |
| ExC-4 | 0.10 |
| ExC-5 | 0.020 |
| ExC-6 | 0.010 |
| Cpd-2 | 0.025 |
| HBS-1 | 0.10 |
| Gelatin | 0.87 |
| Fourth Layer: Middle Sensitivity Red-Sensitive Emulsion Layer | |
| Silver Iodobromide Emulsion C | 0.70 as silver |
| ExS-1 | $4.0 \times 10^{-4}$ |
| ExS-2 | $1.6 \times 10^{-5}$ |
| ExS-3 | $5.6 \times 10^{-4}$ |
| ExC-1 | 0.13 |
| ExC-2 | 0.060 |
| ExC-3 | 0.0070 |
| ExC-4 | 0.090 |
| ExC-5 | 0.015 |
| ExC-6 | 0.0070 |
| Cpd-2 | 0.023 |
| HBS-1 | 0.10 |
| Gelatin | 0.75 |
| Fifth Layer: High Sensitivity Red-Sensitive Emulsion Layer | |
| Silver Iodobromide Emulsion D | 1.40 as silver |

-continued

| | |
|---|---|
| ExS-1 | $2.0 \times 10^{-4}$ |
| ExS-2 | $1.0 \times 10^{-4}$ |
| ExS-3 | $3.8 \times 10^{-4}$ |
| ExC-1 | 0.10 |
| ExC-3 | 0.045 |
| ExC-6 | 0.020 |
| ExC-7 | 0.010 |
| Cpd-2 | 0.050 |
| HBS-1 | 0.22 |
| HBS-2 | 0.050 |
| Gelatin | 1.10 |
| Sixth Layer: Interlayer | |
| Cpd-1 | 0.090 |
| Solid Dispersion Dye ExF-4 | 0.030 |
| HBS-1 | 0.050 |
| Polyethyl Acrylate Latex | 0.15 |
| Gelatin | 1.10 |
| Seventh Layer: Low Sensitivity Green-Sensitive Emulsion Layer | |
| Silver Iodobromide Emulsion E | 0.15 as silver |
| Silver Iodobromide Emulsion F | 0.10 as silver |
| Silver Iodobromide Emulsion G | 0.10 as silver |
| ExS-4 | $3.0 \times 10^{-5}$ |
| ExS-5 | $2.1 \times 10^{-4}$ |
| ExS-6 | $8.0 \times 10^{-4}$ |
| ExM-2 | 0.33 |
| ExM-3 | 0.086 |
| ExY-1 | 0.015 |
| HBS-1 | 0.30 |
| HBS-3 | 0.010 |
| Gelatin | 0.73 |
| Eighth Layer: Middle Sensitivity Green-Sensitive Emulsion Layer | |
| Silver Iodobromide Emulsion H | 0.80 as silver |
| ExS-4 | $3.0 \times 10^{-5}$ |
| ExS-5 | $2.2 \times 10^{-4}$ |
| ExS-6 | $8.6 \times 10^{-4}$ |
| ExC-8 | 0.010 |
| ExM-2 | 0.10 |
| ExM-3 | 0.025 |
| ExY-1 | 0.018 |
| ExY-4 | 0.010 |
| ExY-5 | 0.040 |
| HBS-1 | 0.13 |
| HBS-3 | $4.0 \times 10^{-3}$ |
| Gelatin | 0.80 |
| Ninth Layer: High Sensitivity Green-Sensitive Emulsion Layer | |
| Silver Iodobromide Emulsion I | 1.25 as silver |
| ExS-4 | $3.5 \times 10^{-5}$ |
| ExS-5 | $8.3 \times 10^{-5}$ |
| ExS-6 | $3.2 \times 10^{-4}$ |
| ExC-1 | 0.010 |
| ExM-1 | 0.020 |
| ExM-4 | 0.025 |
| ExM-5 | 0.040 |
| Cpd-3 | 0.040 |
| HBS-1 | 0.25 |
| Polyethyl Acrylate Latex | 0.15 |
| Gelatin | 1.33 |
| Tenth Layer: Yellow Filter Layer | |
| Yellow Colloidal Silver | 0.015 as silver |
| Cpd-1 | 0.16 |
| Solid Dispersion Dye ExF-5 | 0.060 |
| Solid Dispersion Dye ExF-6 | 0.060 |
| Oil-Soluble Dye ExF-7 | 0.010 |
| HBS-1 | 0.60 |
| Gelatin | 0.60 |
| Eleventh Layer: Low Sensitivity Blue-Sensitive Emulsion Layer | |
| Silver Iodobromide Emulsion J | 0.09 as silver |
| Silver Iodobromide Emulsion K | 0.09 as silver |
| ExS-7 | $7.6 \times 10^{-4}$ |
| ExC-8 | $7.1 \times 10^{-3}$ |
| ExY-1 | 0.050 |
| ExY-2 | 0.22 |
| ExY-3 | 0.50 |

-continued

| | |
|---|---|
| ExY-4 | 0.020 |
| Cpd-2 | 0.10 |
| HBS-1 | 0.28 |
| Gelatin | 1.20 |
| Twelfth Layer: High Sensitivity Blue-Sensitive Emulsion Layer | |
| Silver Iodobromide Emulsion L | 1.00 as silver |
| ExS-7 | $4.0 \times 10^{-4}$ |
| ExY-2 | 0.07 |
| ExY-3 | 0.13 |
| ExY-4 | 0.010 |
| Cpd-2 | 0.10 |
| Cpd-3 | $1.0 \times 10^{-3}$ |
| HBS-1 | 0.070 |
| Gelatin | 0.70 |
| Thirteenth Layer: First Protective Layer | |
| UV-1 | 0.19 |
| UV-2 | 0.075 |
| UV-3 | 0.065 |
| F-18 | 0.022 |
| F-19 | 0.012 |
| F-20 | 0.002 |
| F-21 | 0.002 |
| HBS-1 | $5.0 \times 10^{-2}$ |
| HBS-4 | $5.0 \times 10^{-2}$ |
| Gelatin | 1.8 |
| Fourteenth Layer: Second Protective Layer | |
| Silver Iodobromide Emulsion M | 0.10 as silver |
| H-1 | 0.40 |
| B-1 (diameter: 1.7 μm) | $5.0 \times 10^{-2}$ |
| B-2 (diameter: 1.7 μm) | 0.15 |
| B-3 | 0.13 |
| S-1 | 0.20 |
| Gelatin | 0.70 |

Further, W-1 to W-3, B-4 to B-6, F-1 to F-17, iron salt, lead salt, gold salt, platinum salt, palladium salt, iridium salt and rhodium salt were appropriately included in each layer to improve storage stability, processing properties, pressure resistance, fungicidal and biocidal properties, antistatic properties and coating properties.

(2) Emulsions A to L were gold, sulfur, and selenium sensitized, respectively, in the presence of the spectral sensitizing dyes which are described at each light-sensitive layer and sodium thiocyanate according to the examples of JP-A-3-237450 (corresponding to EP-A-443453).

(3) Low molecular weight gelatin was used in the preparation of the tabular grains according to the examples of JP-A-1-158426.

(4) In tabular grains, there were observed such dislocation lines as disclosed in JP-A-3-237450 (corresponding to EP-A-443453), using a high pressure electron microscope.

(5) Emulsion L comprises double structure grains containing an internal high iodide core as disclosed in JP-A-60-143331.

Preparation of Dispersion of Organic Solid Dispersion Dye

ExF-3 shown below was dispersed according to the following method. That is, water and 200 g of Pluronic F88 (ethylene oxide/propylene oxide block copolymer) manufactured by BASF Co. were added to 1,430 g of a wet cake of the dye containing 30% of methanol, and stirred to obtain a slurry having 6% dye concentration. Next, 1,700 ml of zirconia beads having an average diameter of 0.5 mm were filled in an ultravisco mill (UVM-2) manufactured by Imex Co., the slurry was passed and the content was pulverized at a peripheral speed of about 10 m/sec and discharge amount of 0.5 l/min for 8 hours. Beads were removed by filtration, water was added to dilute the dispersion to dye concentration of 3%, then heated at 90° C. for 10 hours for stabilization. The average grain size of the obtained fine grains of the dye was 0.60 μm and the extent of distribution of grain sizes (standard deviation of grain sizes×100/average grain size) was 18%.

TABLE 1

| Emulsion | Average AgI Content (%) | Variation Coefficient of the AgI Content among Grains (%) | Average Grain Size Corresponding to Sphere (μm) | Variation Coefficient of the Grain Size (%) | Projected Area Diameter Corresponding to (μm) Circle | Diameter/ Thickness Ratio |
|---|---|---|---|---|---|---|
| A | 1.7 | 10 | 0.46 | 15 | 0.56 | 5.5 |
| B | 3.5 | 15 | 0.57 | 20 | 0.78 | 4.0 |
| C | 8.9 | 25 | 0.66 | 25 | 0.87 | 5.8 |
| D | 8.9 | 18 | 0.84 | 26 | 1.03 | 3.7 |
| E | 1.7 | 10 | 0.46 | 15 | 0.56 | 5.5 |
| F | 3.5 | 15 | 0.57 | 20 | 0.78 | 4.0 |
| G | 8.8 | 25 | 0.61 | 23 | 0.77 | 4.4 |
| H | 8.8 | 25 | 0.61 | 23 | 0.77 | 4.4 |
| I | 8.9 | 18 | 0.84 | 26 | 1.03 | 3.7 |
| J | 1.7 | 10 | 0.46 | 15 | 0.50 | 4.2 |
| K | 8.8 | 18 | 0.64 | 23 | 0.85 | 5.2 |
| L | 8.8 | 17 | 0.90 | 20 | 1.20 | 7.0 |
| M | 1.0 | — | 0.07 | 15 | — | 1 |

In Table 1:

(1) Emulsions G to L were reduction sensitized during preparation of the grains using thiourea dioxide and thiosulfonic acid according to the examples of JP-A-2-191938 (corresponding to U.S. Pat. No. 5,061,614).

Solid dispersions of ExF-4, ExF-5 and ExF-6 were obtained in the same manner. The average grain sizes of fine grains of the dyes were 0.45 μm, 0.54 μm and 0.52 μm, respectively. ExF-2 was dispersed according to the micro-precipitation dispersion method by pH shift disclosed in the example of JP-A-3-182743. The average grain size of fine grains of the dye was 0.05 μm.

ExC-1
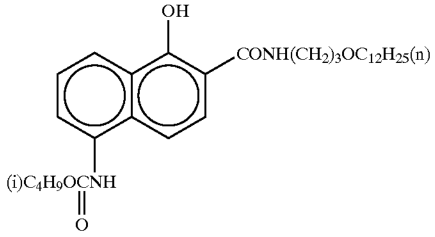
ExC-2
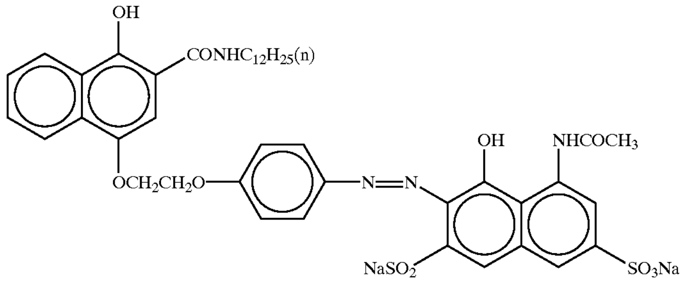
ExC-3
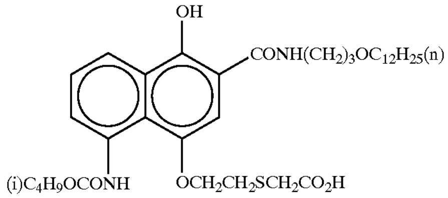
ExC-4
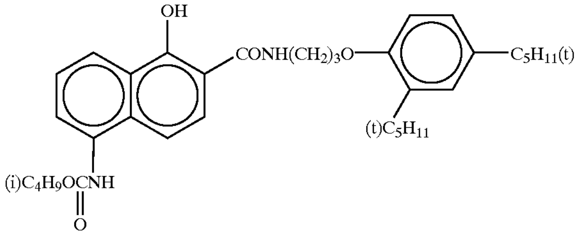
ExC-5
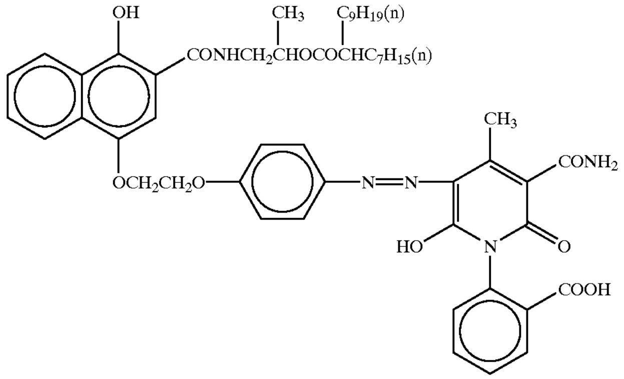

-continued
ExC-6
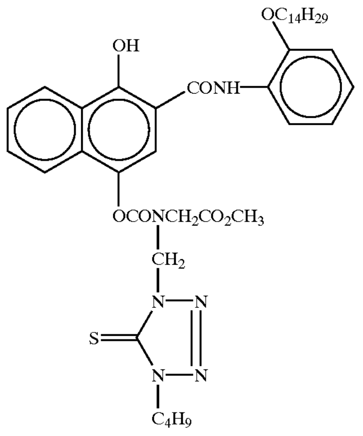
ExC-7
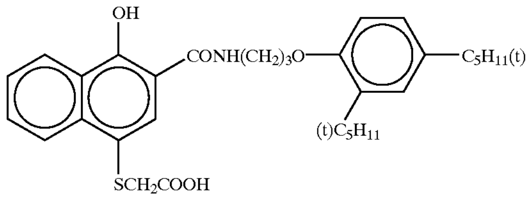
ExC-8
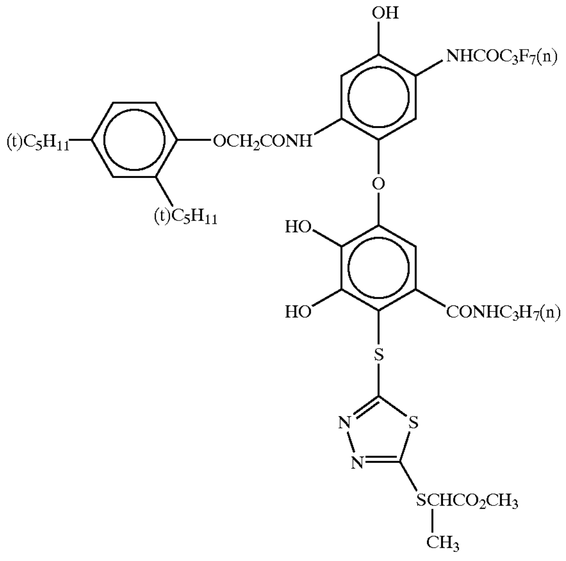
ExM-1
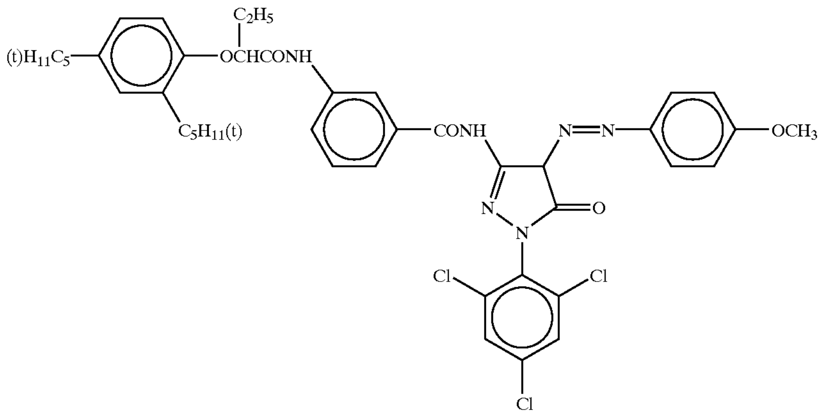

-continued
ExM-2
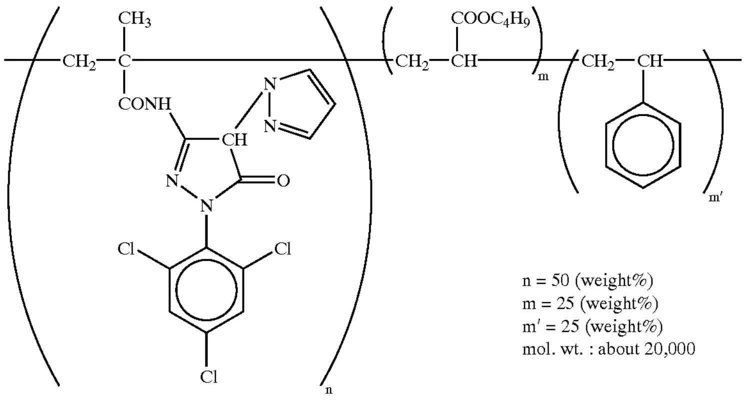
n = 50 (weight%)
m = 25 (weight%)
m' = 25 (weight%)
mol. wt. : about 20,000
ExM-3
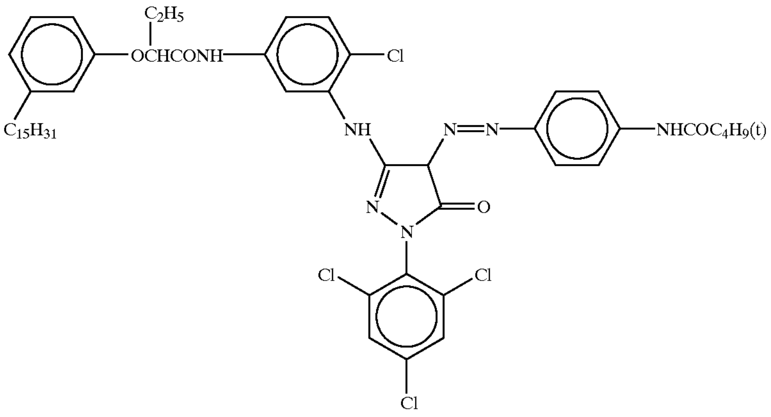
ExM-4
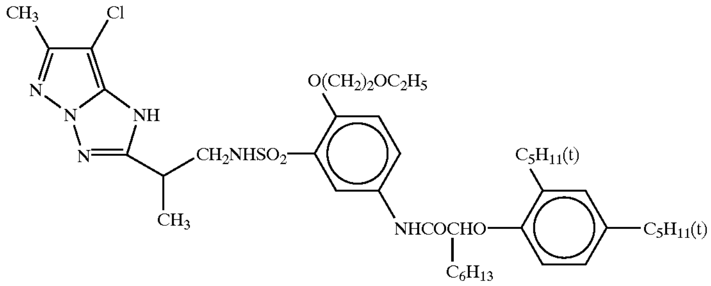
ExM-5
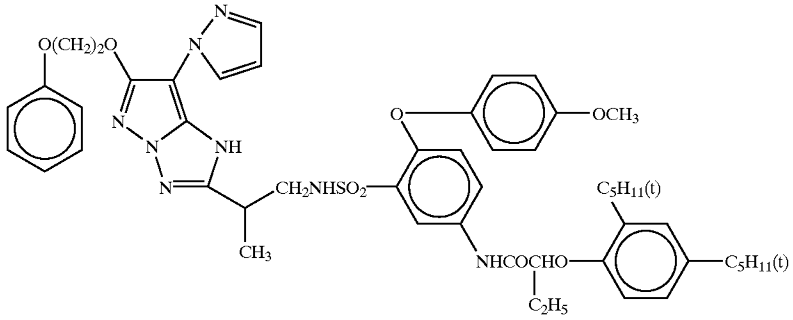

-continued
ExY-1
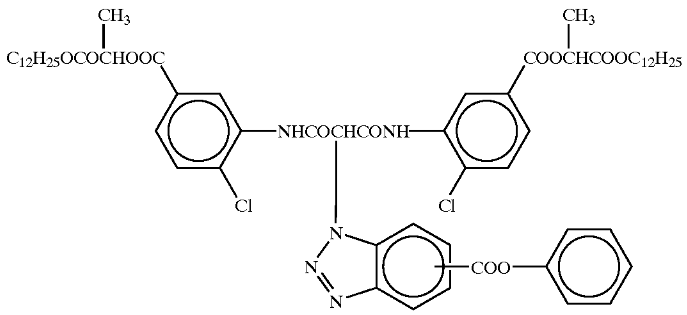
ExY-2
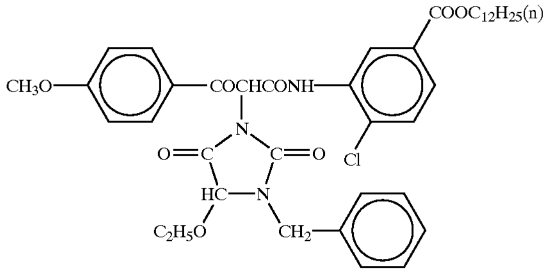
ExY-3
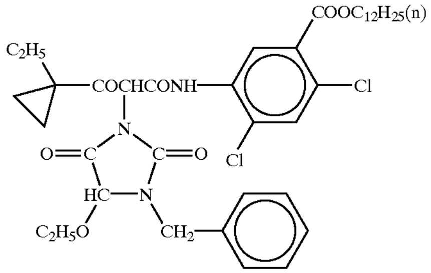
ExY-4
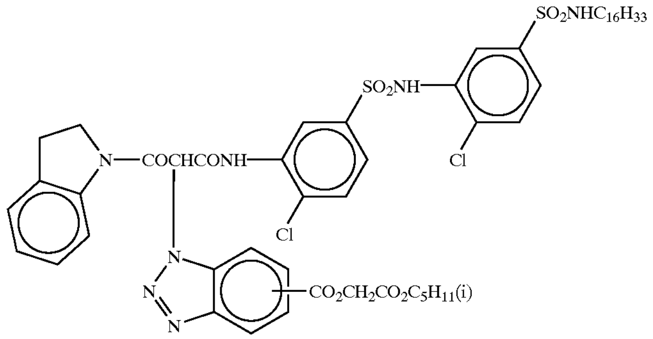
ExY-5
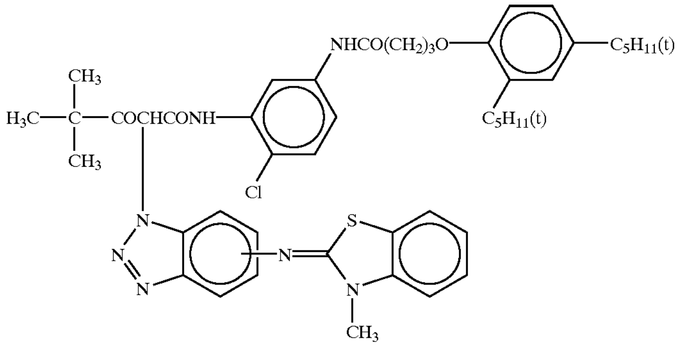

-continued
ExF-1
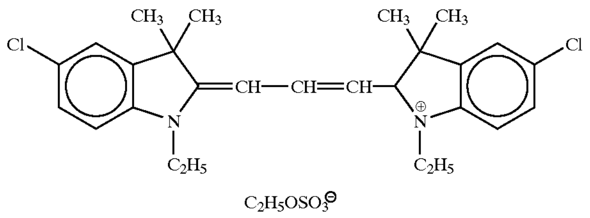
ExF-2
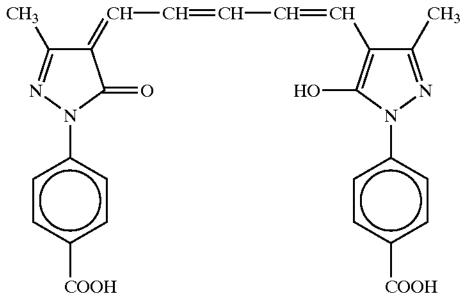
ExF-3
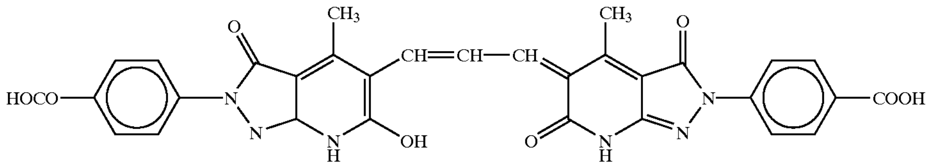
ExF-4
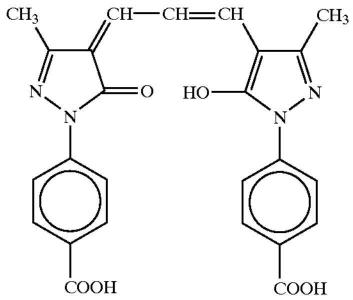
ExF-5
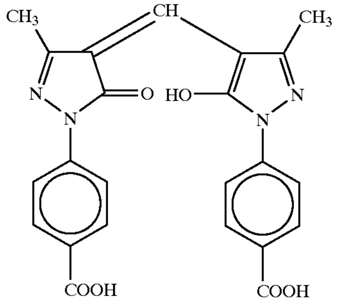
ExF-6
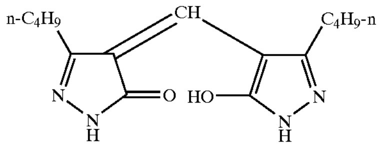

-continued
ExF-7
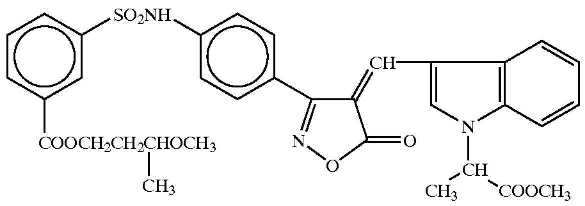
Cpd-1
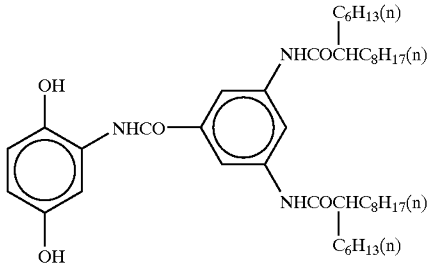
Cpd-2
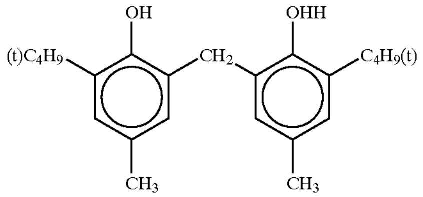
Cpd-3
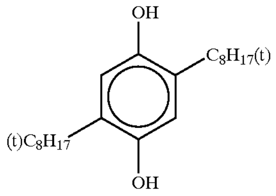
UV-1
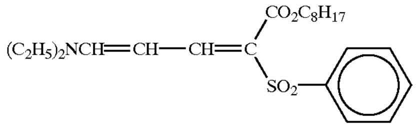
UV-2
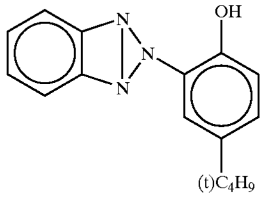
UV-3
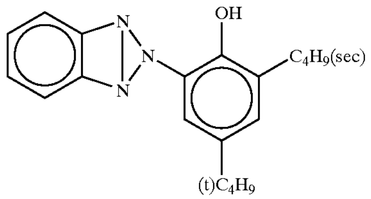
HBS-1
Tricesyl Phosphate
HBS-2
Di-n-butyl Phthalate -continued
HBS-3
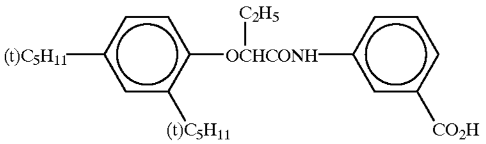
HB2-4
Tri (2-ethylhexyl) Phosphate
ExS-1
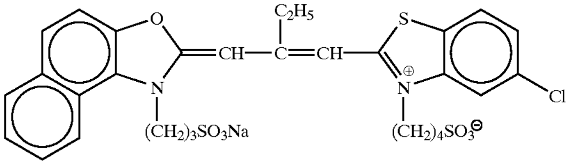
ExS-2
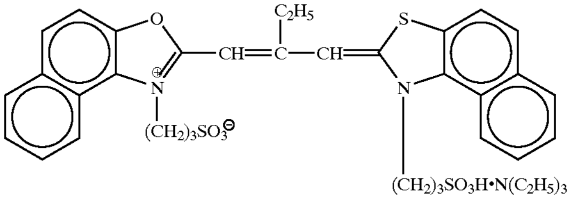
ExS-3
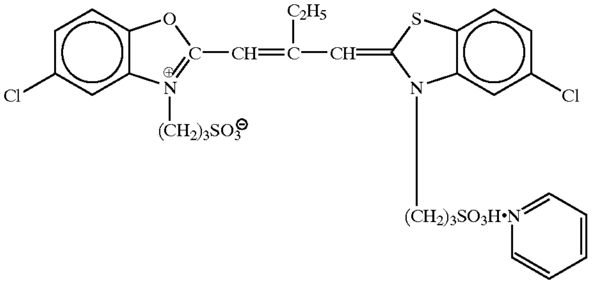
ExS-4
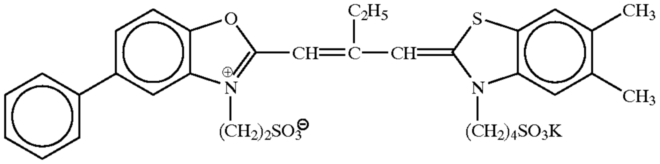
ExS-5
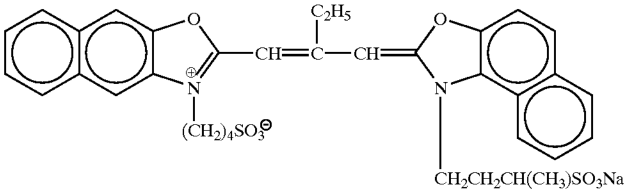
ExS-6
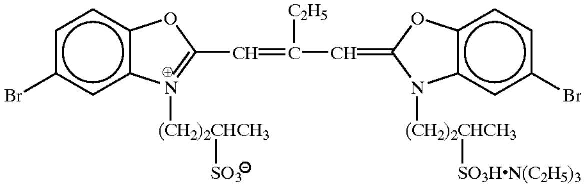
ExS-7
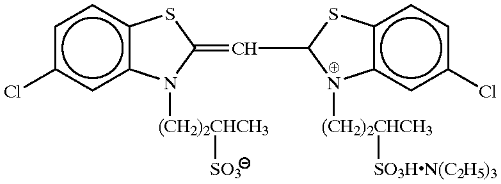

-continued
S-1
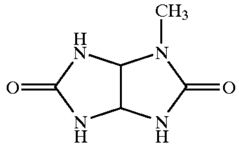
H-1
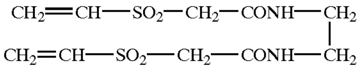
B-1
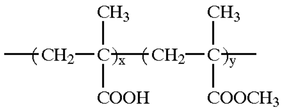
x/y = 10/90 (weight ratio)
average molecular weight:
about 35,000
B-2
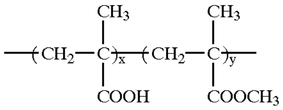
x/y = 40/60 (weight ratio)
average molecular weight:
about 20,000
B-3
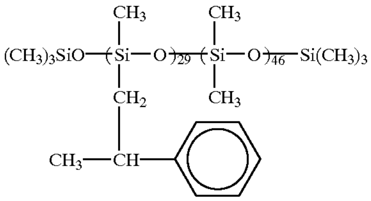
(weight ratio)
average molecular weight:
about 8,000
B-4
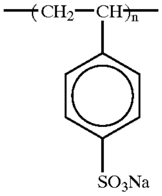
average molecular weight:
about 750,000
(n = an integer)
B-5
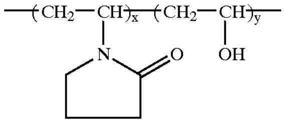
x/y = 70/30 (weight ratio)
average molecular weight:
about 17,000
B-6
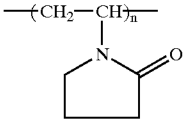
average molecular weight:
about 10,000
(n = an integer)

-continued
W-1
$C_8F_{17}SO_2NHCH_2CH_2CH_2OCH_2CH_2\overset{\ominus}{N}(CH_3)_3$
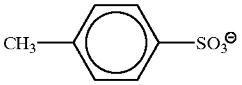
W-2
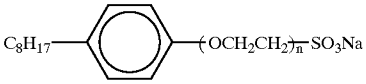
n = 2 ~ 4
W-3
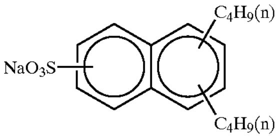
F-1
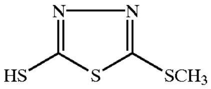
F-2
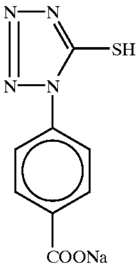
F-3
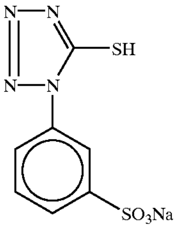
F-4
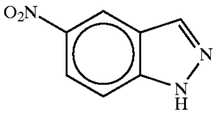
F-5
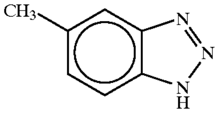
F-6
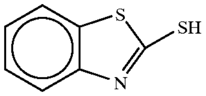
F-7
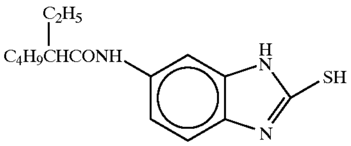

-continued
F-8
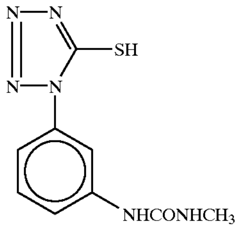
F-9
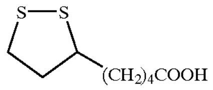
F-10
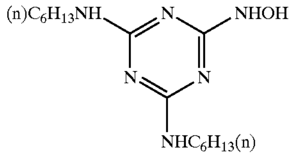
F-11
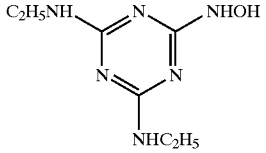
F-12
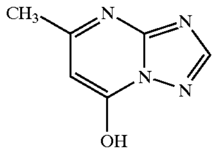
F-13
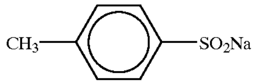
F-14
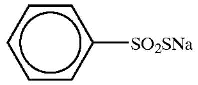
F-15
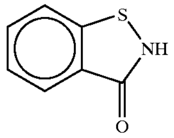
F-16
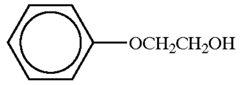
F-17
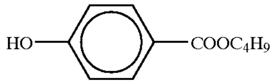
F-18
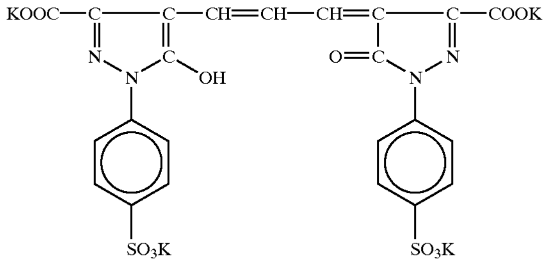

-continued

F-19

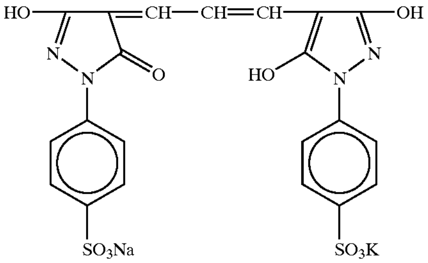

F-20

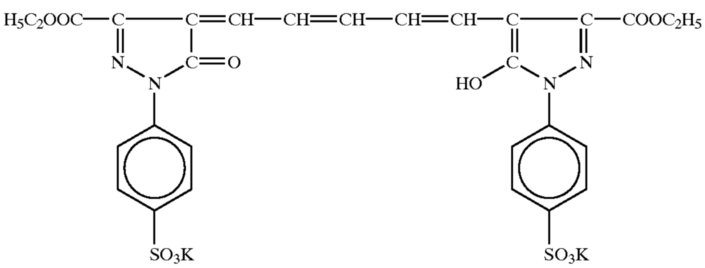

F-21

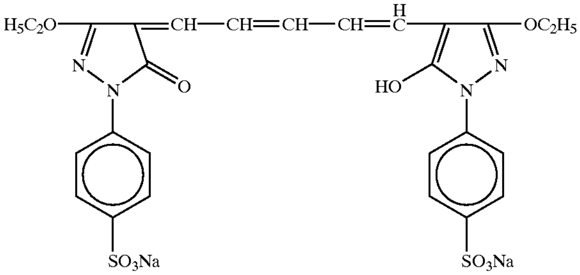

Preparation of Sample Nos. 102 to 122

Sample Nos. 102 to 122 were prepared in the same manner as the preparation of Sample No. 101 except that the compound of the present invention or a comparative compound was added to the ninth layer of each sample as shown in Table 2.

TABLE 2

| Sample No. | Compound according to the Invention: Kind | Amount Added* (mol) | Storage Stability of Latent Image (fluctuation in photographic characteristics) | Change in Fog with the Lapse of Time |
|---|---|---|---|---|
| 101 (Comparison) | — | — | +0.15 | +0.15 |
| 102 (Comparison) | Comparative Compound A | $5 \times 10^{-3}$ | +0.03 | +0.02 |
| 103 (Comparison) | Comparative Compound A | $1 \times 10^{-4}$ | +0.15 | +0.13 |
| 104 (Invention) | 2 | $5 \times 10^{-3}$ | +0.03 | +0.02 |
| 105 (Invention) | 2 | $1 \times 10^{-4}$ | +0.03 | +0.02 |
| 106 (Comparison) | Comparative Compound B | $5 \times 10^{-3}$ | +0.04 | +0.03 |
| 107 (Comparison) | Comparative Compound B | $1 \times 10^{-4}$ | +0.14 | +0.15 |
| 108 (Invention) | 22 | $5 \times 10^{-3}$ | +0.04 | +0.04 |
| 109 (Invention) | 22 | $1 \times 10^{-4}$ | +0.08 | +0.04 |
| 110 (Comparison) | Comparative Compound C | $5 \times 10^{-3}$ | +0.03 | +0.02 |
| 111 (Comparison) | Comparative Compound C | $1 \times 10^{-4}$ | +0.15 | +0.15 |
| 112 (Invention) | 27 | $5 \times 10^{-3}$ | +0.06 | +0.03 |

TABLE 2-continued

| Sample No. | Compound according to the Invention: Kind | Amount Added* (mol) | Storage Stability of Latent Image (fluctuation in photographic characteristics) | Change in Fog with the Lapse of Time |
|---|---|---|---|---|
| 113 (Invention) | 27 | $1 \times 10^{-4}$ | +0.07 | +0.07 |
| 114 (Comparison) | Comparative Compound D | $5 \times 10^{-3}$ | +0.02 | +0.02 |
| 115 (Comparison) | Comparative Compound D | $1 \times 10^{-4}$ | +0.14 | +0.15 |
| 116 (Invention) | 30 | $5 \times 10^{-3}$ | +0.05 | +0.03 |
| 117 (Invention) | 30 | $1 \times 10^{-4}$ | +0.05 | +0.06 |
| 118 (Invention) | 32 | $5 \times 10^{-4}$ | +0.04 | +0.02 |
| 119 (Invention) | 32 | $1 \times 10^{-4}$ | +0.09 | +0.06 |
| 120 (Invention) | 7 | $1 \times 10^{-4}$ | +0.04 | +0.02 |
| 121 (Invention) | 1 | $1 \times 10^{-4}$ | +0.03 | +0.02 |
| 122 (Invention) | 3 | $1 \times 10^{-4}$ | +0.03 | +0.02 |

*mol number per mol of the silver halide in the same layer

Comparative Compound A

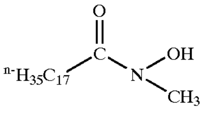

-continued

Comparative Compound B

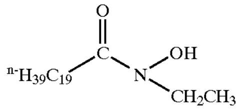

Comparative Compound C

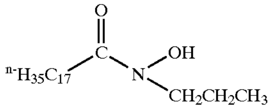

Comparative Compound D

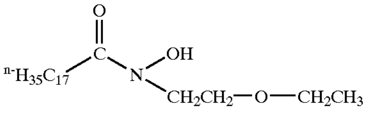

Evaluation of Fluctuation in Photographic Characteristics from Photographing Until Development Processing After each sample was wedgewise exposed by white light, one sample was allowed to stand under conditions of 50° C., 58% RH for 8 days, and the other was stored in a freezer, then each sample was development processed according to the following processing step.

With each sample, the change of the density at the exposure amount of the magenta image of the sample stored in a freezer giving the density of minimum density +1.0 was compared, and (the density of the sample after being stored at 50° C.) minus (the density of the sample after being stored in a freezer) was determined and this was taken as the criterion of the evaluation of fluctuation in photographic characteristics from photographing until development processing of a photographic material, that is, the evaluation value of the storage stability of a latent image. The smaller the value, the larger is the improving effect of the storage stability of the latent image.

Evaluation of Fog with the Lapse of Time

One of each sample was allowed to stand at 45° C., 58% RH for 15 days and the other was stored in a freezer and subjected to the same exposure and development processing as above, and fog with the lapse of time was evaluated by the difference in minimum densities of the green-sensitive layer.

The results obtained are shown in Table 2.

Each processing was conducted using an automatic processor FP-360B manufactured by Fuji Photo Film Co., Ltd. according to the following step. Further, the processor was modified so that the overflow from the bleaching bath was discharged to the waste solution tank not to flow to the after bath. FP-360B processor carried the evaporation correcting means disclosed in Hatsumei Kyokai Kokai Giho 94-4992.

The processing step and the composition of each processing solution are shown below.

Processing Step

| Step | Processing Time | Processing Temperature (° C.) | Replenishment Rate* (ml) | Tank Capacity (liter) |
|---|---|---|---|---|
| Color Development | 3 min 5 sec | 38.0 | 20 | 17 |
| Bleaching | 50 sec | 38.0 | 5 | 5 |
| Fixing (1) | 50 sec | 38.0 | — | 5 |
| Fixing (2) | 50 sec | 38.0 | 8 | 5 |
| Washing | 30 sec | 38.0 | 17 | 3.5 |
| Stabilization (1) | 20 sec | 38.0 | — | 3 |
| Stabilization (2) | 20 sec | 38.0 | 15 | 3 |
| Drying | 1 min 30 sec | 60 | | |

*Replenishment rate: per 1.1 meter of 35 mm wide photographic material (corresponding to a 24 Ex. film)

Stabilization was conducted in a countercurrent system from (2) to (1), and the overflow from the washing tank was all introduced into the fixing tank (2). Fixation was also conducted in a countercurrent system and fixing tanks were connected by countercurrent piping from (2) to (1). Further, the amount of carryover of the developing solution into the bleaching step, the amount of carryover of the bleaching solution to the fixing step, and the amount of carryover of the fixing solution to the washing step were 2.5 ml, 2.0 ml and 2.0 ml per 1.1 meter of 35 mm wide photographic material, respectively. Further, the crossover time was 6 seconds in each case, and this tire is included in the processing time of the previous step.

Open areas of the above processor were 100 $cm^2$ with the color developing solution, 120 $cm^2$ with the bleaching solution and about 100 $cm^2$ with each of other processing solutions.

The composition of each processing solution is described below.

| | Tank Solution (g) | Replenisher (g) |
|---|---|---|
| Color Developing Solution | | |
| Diethylenetriaminepentaacetic Acid | 2.0 | 2.0 |
| 1-Hydroxyethylidene-1,1-diphosphonic Acid | 2.0 | 2.0 |
| Sodium Sulfite | 3.9 | 5.3 |
| Potassium Carbonate | 37.5 | 39.0 |
| Potassium Bromide | 1.4 | 0.4 |
| Potassium Iodide | 1.3 mg | — |
| Disodium N,N-Bis(sulfonatoethyl)hydroxylamine | 2.0 | 2.0 |
| Hydroxylamine Sulfate | 2.4 | 3.3 |
| 2-Methyl-4-[N-ethyl-N-(β-hydroxyethyl) amino]aniline Sulfate | 4.5 | 6.4 |
| Water to make | 1.0 l | 1.0 l |
| pH (adjusted with potassium hydroxide and sulfuric acid) | 10.05 | 10.18 |
| Bleaching Solution | | |
| Ammonium 1,3-Diaminopropanetetraacetato Ferrate Monohydrate | 118 | 180 |
| Ammonium Bromide | 80 | 115 |
| Ammonium Nitrate | 14 | 21 |
| Succinic Acid | 40 | 60 |
| Maleic Acid | 33 | 50 |
| Water to make | 1.0 l | 1.0 l |
| pH (adjusted with aqueous ammonia) | 4.4 | 4.0 |
| Fixing Solution | | |
| Ammonium Methanesulfinate | 10 | 30 |

-continued

| | Tank Solution (g) | Replenisher (g) |
|---|---|---|
| Ammonium Methanethiosulfonate | 4 | 12 |
| Aqueous Ammonium Thiosulfate Solution (700 g/liter) | 280 ml | 840 ml |
| Imidazole | 7 | 20 |
| Ethylenediaminetetraacetic Acid | 15 | 45 |
| Water to make | 1.0 l | 1.0 l |
| pH (adjusted with aqueous ammonia and acetic acid) | 7.4 | 7.45 |

Washing Water

City water was passed through a mixed bed column packed with an H-type strongly acidic cation exchange resin (Amberlite IR-120B of Rohm & Haas) and an OH-type strongly basic anion exchange resin (Amberlite IR-400 of Rohm & Haas) and treated so as to reduce the calcium ion and magnesium ion concentrations to 3 mg/liter or less, subsequently 20 mg/liter of sodium isocyanurate dichloride and 150 mg/liter of sodium sulfate were added thereto. The pH of this washing water was in the range of from 6.5 to 7.5.

Stabilizing Solution (Replenisher Equals Tank Solution)

| | (unit: g) |
|---|---|
| Sodium p-Toluenesulfinate | 0.03 |
| Polyoxyethylene-p-monononylphenyl Ether (average polymerization degree: 10) | 0.2 |
| Disodium Ethylenediaminetetraacetate | 0.05 |
| 1,2,4-Triazole | 1.3 |
| 1,4-Bis(1,2,4-triazol-1-ylmethyl)-piperazine | 0.75 |
| 1,2-Benzisothiazolin-3-one | 0.10 |
| Water to make | 1.0 l |
| pH | 8.5 |

As is apparent from the results in Table 2, the compounds of the present invention show the effects of improving storage stability of a latent image and change in fog with the lapse of time with a reduced addition amount. With respect to Comparative Compounds A to D, the improving effects extremely lower by reducing the addition amount, on the contrary, the compounds of the present invention are less in dependence on the addition amount, and it can be seen that Compounds 1, 2, 3 and 7 of the present invention, in particular, provide the sufficient improving effects with a reduced addition amount.

Comparative Compounds A to D are oil-soluble and it is presumed that they exist uniformly in an oil droplet comprising a coupler and a high boiling point organic solvent in an emulsion. On the contrary, the compounds of the present invention have the structure of being easily oriented locally on the surface of an oil droplet by introducing a polar group into a reduction mother nucleus.

These compounds of the present invention are supposed to control the decomposition or the growth of a latent subimage nucleus or a fogging nucleus in a silver halide grain or to capture organic radicals which are generated during aging of a photographic material and hinder from contacting to silver halide grains. In either case, a reduction mother nucleus is advantageous to be contact with or exist near silver halide. Accordingly, the existence of the compound locally on the surface of an oil droplet is effective for obtaining a useful effect with a reduced amount.

EXAMPLE 2

Preparation of Sample No. 201

Sample No. 201 was prepared in the same manner as the preparation of Sample No. 101 in Example 1, except for replacing the support with the support prepared as follows.

1) Support

The support which was used in Example 2 was prepared as follows.

100 weight parts of polyethylene-2,6-naphthalate polymer and 2 weight parts of Tinuvin P. 326 (product of Ciba-Geigy), as an ultraviolet absorber, were dried, then melted at 300° C., subsequently, extruded through a T-type die, and stretched 3.3 times in a machine direction at 140° C. and then 3.3 times in a transverse direction at 130° C., and further thermal fixed for 6 seconds at 250° C. and the PEN film having the thickness of 90 μm was obtained. Appropriate amounts of blue dyes, magenta dyes and yellow dyes were added to the PEN film (I-1, I-4, I-6, I-24, I-26, I-27 and II-5 disclosed in Kokai-Giho, Kogi No. 54-6023). Further, the film was wound on to a stainless steel spool having a diameter of 20 cm and provided heat history at 110° C. for 48 hours to obtain a support reluctant to get curling habit.

2) Coating of Undercoat Layer

After both surfaces of the above support were subjected to corona discharge, UV discharge and glow discharge treatments, on one side of the support an undercoat solution having the following composition was coated (10 cc/$m^2$, using a bar coater): 0.1 g/$m^2$ of gelatin, 0.01 g/$m^2$ of sodium α-sulfo-di-2-ethylhexylsuccinate, 0.04 g/$m^2$ of salicylic acid, 0.2 g/$m^2$ of p-chlorophenol, 0.012 g/$m^2$ of $(CH_2{=}CHSO_2CH_2CH_2NHCO)_2CH_2$, and 0.02 g/$m^2$ of polyamide-epichlorohydrin polycondensation product. The undercoat layer was provided on the hotter side at the time of stretching. Drying was conducted at 115° C. for 6 minutes (the temperature of the roller and transporting device of the drying zone was 115° C.).

3) Coating of Backing Layer

On one side of the above support after undercoat layer coating, an antistatic layer, a magnetic recording layer and a sliding layer each having the following composition were coated as backing layers.

3-1) Coating of Antistatic Layer 0.2 g/$m^2$ of a dispersion of fine grain powder of a stannic oxide-antimony oxide composite having the average grain size of 0.005 μm and specific resistance of 5 Ω.cm (the grain size of the second agglomerate: about 0.08 μm), 0.05 g/$m^2$ of gelatin, 0.02 g/$m^2$ of $(CH_2{=}CHSC_2CH_2CH_2NHCO)_2CH_2$, 0.005 g/$m^2$ of polyoxyethylene-p-nonylphenol (polymerization degree: 10) and 0.22 g/$m^2$ of resorcin were coated.

3-2) Coating of Magnetic Recording Layer 0.06 g/$m^2$ of cobalt-γ-iron oxide which was coating-treated with 3-polyoxyethylene-propyloxytrimethoxysilane (polymerization degree: 15) (15 wt %) (specific surface area: 43 $m^2$/g, major axis: 0.14 μm, minor axis: 0.03 μm, saturation magnetization: 89 emu/g, $Fe^{+2}/Fe^{+3}$ is 6/94, the surface was treated with 2 wt %, respectively, based on the iron oxide, of aluminum oxide and silicon oxide), 1.2 /$m^2$ of diacetyl cellulose (dispersion of the iron oxide was carried out using an open kneader and a sand mill), 0.3 g/$m^2$ of $C_2H_5C[CH_2OCONH—C_6H_3(CH_3)NCO]_3$ as a curing agent, with acetone, methyl ethyl ketone, cyclohexanone and dibutyl phthalate as solvents, were coated on the above support with a bar coater to obtain a magnetic recording layer having the film thickness of 1.2 μm. 50 mg/$m^2$ of $C_6H_{13}CH(OH)C_{10}H_{20}COOC_{40}H_{81}$ as a sliding agent, and as matting agents, silica grains (1.0 μm) and an aluminum oxide abrasive (0.20 μm and 1.0 μm) treated and coated with 3-polyoxyethylene-propyloxytrimethoxysilane (polymerization degree: 15) (15 wt %) were added each in an amount of 50 mg/m$^2$ and 10 mg/m$^2$, respectively. Drying was conducted at 115° C. for 6 minutes (the temperature of the roller and transporting device of the drying zone was 115° C.). The increase of the color density of $D^B$ of the magnetic recording layer by X-light (a blue filter) was about 0.1, and saturation magnetization moment of the magnetic recording layer was 4.2 emu/g, coercive force was 7.3x10$^4$ A/m, and rectangular ratio was 65%.

3-3) Preparation of Sliding Layer

Diacetyl cellulose (25 mg/m$^2$), $C_6H_{13}CH(OH)C_{10}H_{20}COOCl_{40}H_{81}$ (6 mg/m$^2$), and poly(dimethylsiloxane) (B-3) (1.5 mg/m$^2$) were coated. This mixture was dissolved in xylene/propylene monomethyl ether (1/1) by heating at 105° C., and poured into propylene monomethyl ether (10 time amount) at room temperature and dispersed, and further dispersed in acetone (average grain size: 0.01 μm), then added to the coating solution. Drying was conducted at 115° C. for 6 minutes (the temperature of the roller and transporting device of the drying zone was 115° C.). The thus-obtained sliding layer showed excellent capabilities of dynamic friction coefficient of 0.10 (a stainless steel hard ball of 5 mmϕ, load: 100 g, speed: 6 cm/min), static friction coefficient of 0.08 (a clip method), and the sliding property with the surface of the emulsion provided dynamic friction coefficient of 0.15.

The thus prepared photographic material was cut to a size of 24 mm in width and 160 cm in length, and two perforations of 2 mm square at an interval of 5.8 mm were provided 0.7 mm inside from one side width direction in the length direction of the photographic material. The sample provided with this set of two perforations at intervals of 32 mm was prepared and encased in the film cartridge made of plastics as explained in FIG. 1 to FIG. 7 in U.S. Pat. No. 5,296,887.

FM signals were recorded between the above perforations of the sample from the side of the support having the magnetic recording layer using a head capable of in and out of 2,000 turns with head gap of 5 μm at a feed rate of 1,000/s.

Preparation of Sample Nos. 202 to 205

Sample Nos. 202 to 205 were prepared in the same manner as the preparation of Sample No. 201 except that the compound of the present invention was added to the fifth layer of each sample as shown in Table 3.

TABLE 3

| Sample No. | Compound according to the Invention: Kind | Compound according to the Invention: Amount Added* (mol) | Storage Stability of Latent Image (fluctuation in photographic characteristics) | Change in Fog with the Lapse of Time |
|---|---|---|---|---|
| 201 (Comparison) | — | — | +0.13 | +0.12 |
| 202 (Comparison) | Comparative Compound A | 4 × $10^{-3}$ | +0.02 | +0.01 |
| 203 (Comparison) | Comparative Compound A | 8 × $10^{-5}$ | +0.13 | +0.09 |
| 204 (Invention) | 2 | 4 × $10^{-3}$ | +0.03 | +0.01 |
| 205 (Invention) | 2 | 8 × $10^{-5}$ | +0.03 | +0.01 |

*mol number per mol of the silver halide in the same layer

Evaluation of Fluctuation in Photographic Characteristics from Photographing Until Development Processing After each sample was wedgewise exposed by white light, one sample was allowed to stand under conditions of 50° C., 58% RH for 7 days, and the other was stored in a freezer, then each sample was development processed.

With each sample, the change of the density at the exposure amount of the cyan image of the sample stored in a freezer giving the density of minimum density +1.0 was compared, and (the density of the sample after being stored at 50° C.) minus (the density of the sample after being stored in a freezer) was determined and this was taken as the criterion of the evaluation of fluctuation in photographic characteristics from photographing until development processing of a photographic material, that is, the evaluation value of the storage stability of a latent image. The smaller the value, the larger is the improving effect of the storage stability of the latent image.

Evaluation of Fog with the Lapse of Time

One of each sample was allowed to stand at 45° C., 58% RH for 14 days and the other was stored in a freezer and subjected to the same exposure and development processing as above, and fog with the lapse of time was evaluated by the difference in minimum densities of the red-sensitive layer.

The development processing is the same as the processing in Example 1.

The results obtained are shown in Table 3.

As is apparent from the results in Table 3, Compound 2 of the present invention shows to have sufficient improving effects of storage stability of a latent image and change in fog with the lapse of time with a reduced addition amount.

EXAMPLE 3

Preparation of Sample No. 301

A multilayer color photographic material was prepared as Sample No. 301 by coating each layer having the following composition on an undercoated cellulose triacetate film support having the thickness of 127 μm. The numeral corresponding to each component indicates the addition amount per m$^2$. The function of the compounds added is not limited to the use described.

| | |
|---|---|
| First Layer: Antihalation Layer | |
| Black Colloidal Silver | 0.20 g |
| Gelatin | 1.90 g |
| Ultraviolet Absorber U-1 | 0.10 g |
| Ultraviolet Absorber U-3 | 0.040 g |
| Ultraviolet Absorber U-4 | 0.10 g |
| High Boiling Point Organic Solvent Oil-1 | 0.10 g |
| Crystallite Solid Dispersion of Dye E-1 | 0.10 g |
| Second Layer: Interlayer | |
| Gelatin | 0.40 g |
| Compound Cpd-C | 5.0 mg |
| Compound Cpd-J | 5.0 mg |
| Compound Cpd-K | 3.0 g |
| High Boiling Point Organic Solvent Oil-3 | 0.10 g |
| Dye D-4 | 0.80 mg |
| Third Layer: Interlayer | |
| Surface and Interior Fogged Fine Grain Silver Iodobromide Emulsion (average grain size: 0.06 μm, variation coefficient: 18%, AgI content: 1 mol %) | silver amount: 0.050 g |
| Yellow Colloidal Silver | silver amount: 0.030 g |
| Gelatin | 0.40 g |

-continued

| | |
|---|---|
| Fourth Layer: Low Sensitivity Red-Sensitive Emulsion Layer | |
| Emulsion A | silver amount: 0.30 g |
| Emulsion B | silver amount: 0.20 g |
| Gelatin | 0.80 g |
| Coupler C-1 | 0.15 g |
| Coupler C-2 | 0.050 g |
| Coupler C-3 | 0.050 g |
| Coupler C-9 | 0.050 g |
| Compound Cpd-C | 5.0 mg |
| Compound Cpd-J | 5.0 mg |
| High Boiling Point Organic Solvent Oil-2 | 0.10 g |
| Additive P-1 | 0.10 g |
| Fifth Layer: Middle Sensitivity Red-Sensitive Emulsion Layer | |
| Emulsion B | silver amount: 0.20 g |
| Emulsion C | silver amount: 0.30 g |
| Gelatin | 0.80 g |
| Coupler C-1 | 0.20 g |
| Coupler C-2 | 0.050 g |
| Coupler C-3 | 0.20 g |
| High Boiling Point Organic Solvent Oil-2 | 0.10 g |
| Additive P-1 | 0.10 g |
| Sixth Layer: High Sensitivity Red-Sensitive Emulsion Layer | |
| Emulsion D | silver amount: 0.40 g |
| Gelatin | 1.10 g |
| Coupler C-1 | 0.30 g |
| Coupler C-2 | 0.10 g |
| Coupler C-3 | 0.70 g |
| Additive P-1 | 0.10 g |
| Seventh Layer: Interlayer | |
| Gelatin | 0.60 g |
| Additive M-1 | 0.30 g |
| Color Mixing Preventive Cpd-I | 2.6 mg |
| Dye D-5 | 0.020 g |
| Dye D-6 | 0.010 g |
| Compound Cpd-J | 5.0 mg |
| High Boiling Point Organic Solvent Oil-1 | 0.020 g |
| Eighth Layer: Interlayer | |
| Surface and Interior Fogged Silver Iodobromide Emulsion (average grain size: 0.06 μm, variation coefficient: 16%, AgI content: 0.3 mol %) | silver amount: 0.020 g |
| Yellow Colloidal Silver | silver amount: 0.020 g |
| Gelatin | 1.00 g |
| Additive P-1 | 0.20 g |
| Color Mixing Preventive Cpd-A | 0.10 g |
| Compound Cpd-C | 0.10 g |
| Ninth Layer: Low Sensitivity Green-Sensitive Emulsion Layer | |
| Emulsion E | silver amount: 0.10 g |
| Emulsion F | silver amount: 0.20 g |
| Emulsion G | silver amount: 0.20 g |
| Gelatin | 0.50 g |
| Coupler C-7 | 0.20 g |
| Coupler C-8 | 0.20 g |
| Compound Cpd-B | 0.030 g |
| Compound Cpd-D | 0.020 g |
| Compound Cpd-E | 0.020 g |
| Compound Cpd-F | 0.040 g |
| Compound Cpd-J | 10 mg |
| Compound Cpd-L | 0.020 g |
| High Boiling Point Organic Solvent Oil-1 | 0.10 g |
| High Boiling Point Organic Solvent Oil-2 | 0.10 g |
| Tenth Layer: Middle Sensitivity Green-Sensitive Emulsion Layer | |
| Emulsion G | silver amount: 0.30 g |
| Emulsion H | silver amount: 0.10 g |
| Gelatin | 0.60 g |
| Coupler C-4 | 0.10 g |
| Coupler C-7 | 0.20 g |
| Coupler C-8 | 0.10 g |
| Compound Cpd-B | 0.030 g |
| Compound Cpd-D | 0.020 g |
| Compound Cpd-E | 0.020 g |

-continued

| | |
|---|---|
| Compound Cpd-F | 0.050 g |
| Compound Cpd-L | 0.050 g |
| High Boiling Point Organic Solvent Oil-2 | 0.010 g |
| Eleventh Layer: High Sensitivity Green-Sensitive Emulsion Layer | |
| Emulsion I | silver amount: 0.50 g |
| Gelatin | 1.00 g |
| Coupler C-4 | 0.30 g |
| Coupler C-7 | 0.10 g |
| Coupler C-8 | 0.10 g |
| Compound Cpd-B | 0.080 g |
| Compound Cpd-E | 0.020 g |
| Compound Cpd-F | 0.040 g |
| Compound Cpd-K | 5.0 mg |
| Compound Cpd-L | 0.020 g |
| High Boiling Point Organic Solvent Oil-1 | 0.020 g |
| High Boiling Point Organic Solvent Oil-2 | 0.020 g |
| Twelfth Layer: Interlayer | |
| Gelatin | 0.60 g |
| Compound Cpd-L | 0.050 g |
| High Boiling Point Organic Solvent Oil-1 | 0.050 g |
| Thirteenth Layer: Yellow Filter Layer | |
| Yellow Colloidal Silver | silver amount: 0.070 g |
| Gelatin | 1.10 g |
| Color Mixing Preventive Cpd-A | 0.010 g |
| Compound Cpd-L | 0.010 g |
| High Boiling Point Organic Solvent Oil-1 | 0.010 g |
| Crystallite Solid Dispersion of Dye E-2 | 0.050 g |
| Fourteenth Layer: Interlayer | |
| Gelatin | 0.60 g |
| Fifteenth Layer: Low Sensitivity Blue-Sensitive Emulsion Layer | |
| Emulsion J | silver amount: 0.20 g |
| Emulsion K | silver amount: 0.30 g |
| Gelatin | 0.80 g |
| Coupler C-5 | 0.20 g |
| Coupler C-6 | 0.10 g |
| Coupler C-10 | 0.40 g |
| Sixteenth Layer: Middle Sensitivity Blue-Sensitive Emulsion Layer | |
| Emulsion L | silver amount: 0.30 g |
| Emulsion M | silver amount: 0.30 g |
| Gelatin | 0.90 g |
| Coupler C-5 | 0.10 g |
| Coupler C-6 | 0.10 g |
| Coupler C-10 | 0.60 g |
| Seventeenth Layer: High Sensitivity Blue-sensitive Emulsion Layer | |
| Emulsion N | silver amount: 0.20 g |
| Emulsion O | silver amount: 0.20 g |
| Gelatin | 1.20 g |
| Coupler C-5 | 0.10 g |
| Coupler C-6 | 0.10 g |
| Coupler C-10 | 0.60 g |
| High Boiling Point Organic Solvent Oil-2 | 0.10 g |
| Eighteenth Layer: First Protective Layer | |
| Gelatin | 0.70 g |
| Ultraviolet Absorber U-1 | 0.20 g |
| Ultraviolet Absorber U-2 | 0.050 g |
| Ultraviolet Absorber U-5 | 0.30 g |
| Formalin Scavenger Cpd-H | 0.40 g |
| Dye D-1 | 0.15 g |
| Dye D-2 | 0.050 g |
| Dye D-3 | 0.10 g |
| Nineteenth Layer: Second Protective Layer | |
| Colloidal Silver | silver amount: 0.10 mg |
| Fine Grain Silver Iodobromide Emulsion (average grain size: 0.06 μm, AgI content: 1 mol %) | silver amount: 0.10 g |
| Gelatin | 0.40 g |
| Twentieth Layer: Third Protective Layer | |
| Gelatin | 0.40 g |
| Polymethyl Methacrylate | 0.10 g |

-continued

| | |
|---|---|
| (average particle size: 1.5 μm) | |
| Copolymer of Methyl Methacrylate/Acrylic Acid in Proportion of 4/6 | 0.10 g |
| (average particle size: 1.5 μm) | |
| Silicone Oil | 0.030 g |
| Surfactant W-1 | 3.0 mg |
| Surfactant W-2 | 0.030 g |

Further, Additives F-1 to F-8 were added to every emulsion layer in addition to the above components. Moreover, gelatin hardener H-1 and surfactants W-3, W-4, W-5 and W-6 for coating and emulsifying were added to every layer in addition to the above components.

In addition, phenol, 1,2-benzisothiazolin-3-one, 2-phenoxyethanol, phenethyl alcohol, p-benzoic acid butyl ester were added as antibacterial and antifungal agents.

The silver iodobromide emulsions used in Sample No. 301 are as shown in Table 1.

TABLE 4

| Emulsion Name | Characteristics of Grain | Average Grain Size Corresponding to Sphere (μm) | Variation Coefficient (%) | AgI Content (%) |
|---|---|---|---|---|
| A | Monodisperse tetradecahedral grains | 0.28 | 16 | 4.0 |
| B | Monodisperse cubic internal latent image type grains | 0.30 | 10 | 4.0 |
| C | Monodisperse cubic grains | 0.38 | 10 | 5.0 |
| D | Monodisperse tabular grains, average aspect ratio: 4.5 | 0.68 | 8 | 2.0 |
| E | Monodisperse cubic grains | 0.20 | 17 | 4.0 |
| F | Monodisperse tetradecahedral grains | 0.25 | 16 | 4.0 |
| G | Monodisperse cubic internal latent image type grains | 0.40 | 11 | 4.0 |
| H | Monodisperse cubic grains | 0.50 | 9 | 3.5 |
| I | Monodisperse tabular grains, average aspect ratio: 5.0 | 0.80 | 10 | 2.0 |
| J | Monodisperse cubic grains | 0.30 | 18 | 4.0 |
| K | Monodisperse tetradecahedral grains | 0.45 | 17 | 4.0 |
| L | Monodisperse tabular grains, average aspect ratio: 5.0 | 0.55 | 10 | 2.0 |
| M | Monodisperse tabular grains, average aspect ratio: 8.0 | 0.70 | 13 | 2.0 |
| N | Monodisperse tabular grains, average aspect ratio: 6.0 | 1.00 | 10 | 1.5 |
| O | Monodisperse tabular grains, averaqe aspect ratio: 9.0 | 1.20 | 15 | 1.5 |

TABLE 5

Spectral Sensitization of Emulsions A to I

| Emulsion Name | Sensitizing Dye Added | Addition Amount per Mol of Silver Halide (g) |
|---|---|---|
| A | S-2 | 0.025 |
| | S-3 | 0.25 |
| | S-8 | 0.010 |
| B | S-1 | 0.010 |
| | S-3 | 0.25 |
| | S-8 | 0.010 |

TABLE 5-continued

Spectral Sensitization of Emulsions A to I

| Emulsion Name | Sensitizing Dye Added | Addition Amount per Mol of Silver Halide (g) |
|---|---|---|
| C | S-1 | 0.010 |
| | S-2 | 0.010 |
| | S-3 | 0.25 |
| | S-8 | 0.010 |
| D | S-2 | 0.010 |
| | S-3 | 0.20 |
| | S-8 | 0.015 |
| E | S-4 | 0.55 |
| | S-5 | 0.05 |
| F | S-4 | 0.34 |
| | S-5 | 0.06 |
| G | S-4 | 0.25 |
| | S-5 | 0.08 |
| | S-9 | 0.05 |

TABLE 5-continued

Spectral Sensitization of Emulsions A to I

| Emulsion Name | Sensitizing Dye Added | Addition Amount per Mol of Silver Halide (g) |
|---|---|---|
| H | S-4 | 0.20 |
| | S-5 | 0.060 |
| | S-9 | 0.050 |

TABLE 5-continued

Spectral Sensitization of Emulsions A to I

| Emulsion Name | Sensitizing Dye Added | Addition Amount per Mol of Silver Halide (g) |
|---|---|---|
| I | S-4 | 0.035 |
| | S-5 | 0.070 |
| | S-9 | 0.06 |

TABLE 6

Spectral Sensitization of Emulsions J to O

| Emulsion Name | Sensitizing Dye Added | Addition Amount per Mol of Silver Halide (g) |
|---|---|---|
| J | S-6 | 0.050 |
| | S-7 | 0.20 |
| K | S-6 | 0.05 |
| | S-7 | 0.20 |
| L | S-6 | 0.060 |
| | S-7 | 0.22 |
| M | S-6 | 0.050 |
| | S-7 | 0.17 |
| N | S-6 | 0.040 |
| | S-7 | 0.15 |
| O | S-6 | 0.060 |
| | S-7 | 0.22 |

C-1

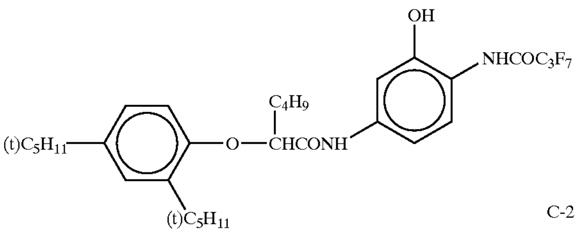

C-2

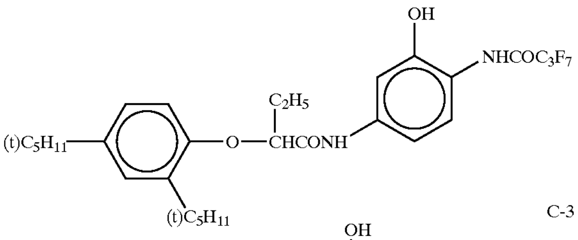

C-3

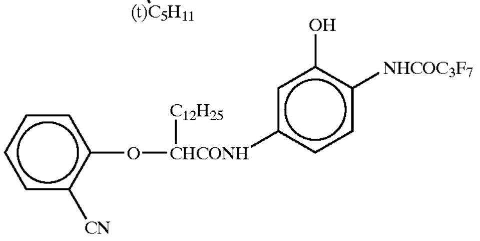

-continued

C-4

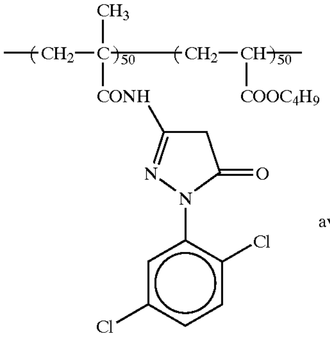

numerals indicate wt%
average molecular weight:
about 25,000

C-5

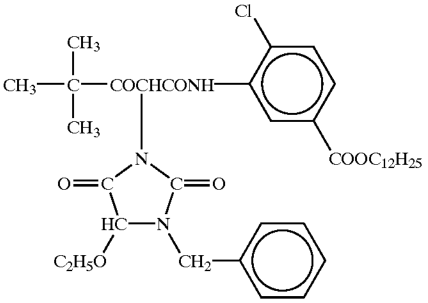

C-6

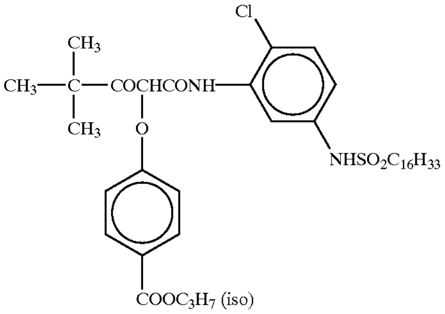

C-7

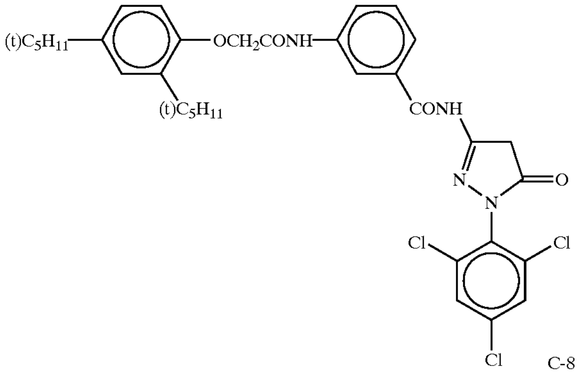

C-8

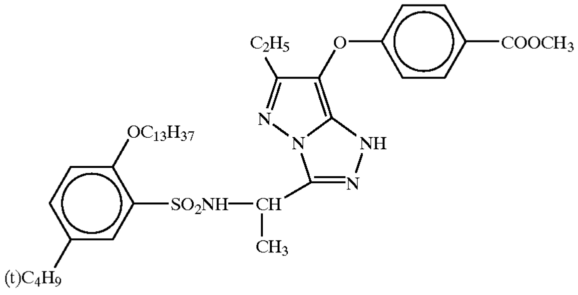

-continued
C-9
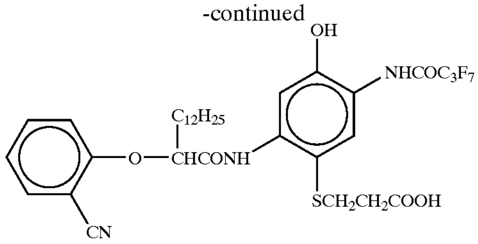
C-10
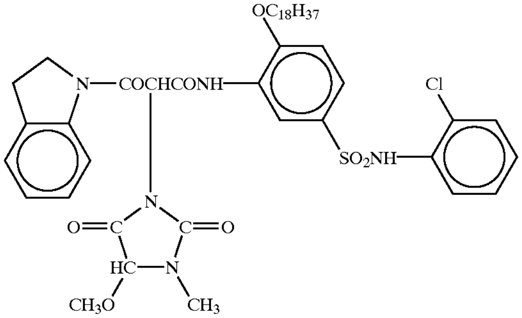
Oil-1
Dibutyl Phthalate
Oil-2
Tricresyl Phosphate
Oil-3
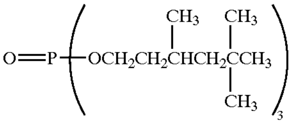
Cpd-A
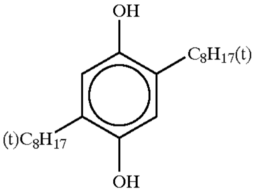
Cpd-B
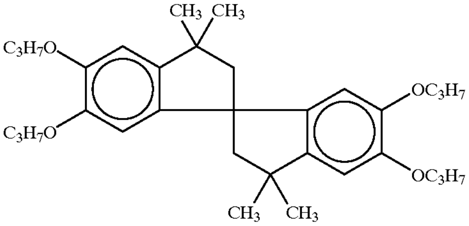
Cpd-C
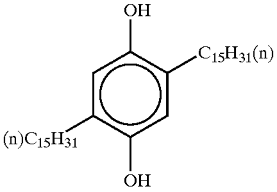
Cpd-D
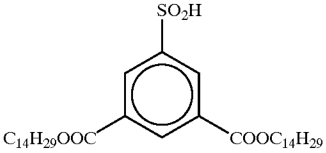
-continued
Cpd-E
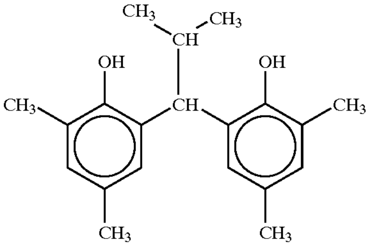
Cpd-F
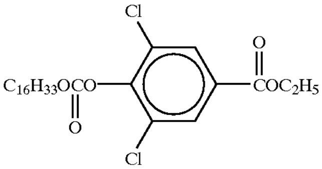
Cpd-H
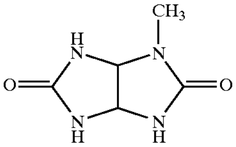
Cpd-I
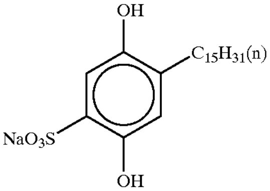
Cpd-J
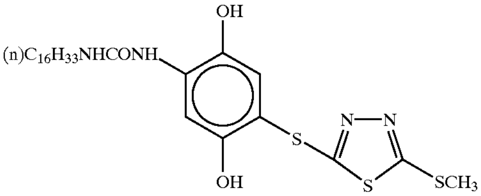
Cpd-K
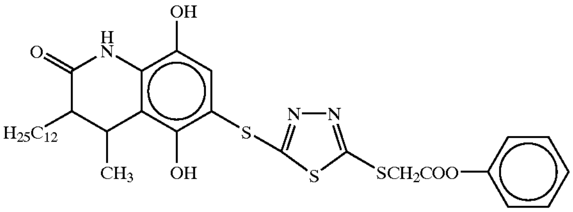
Cpd-L
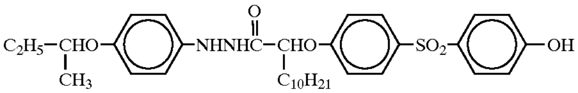
U-1
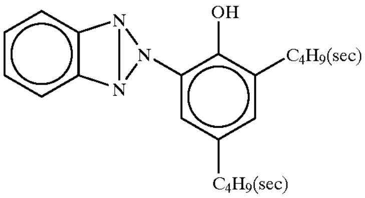

-continued
U-2
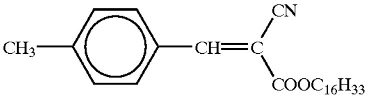
U-3
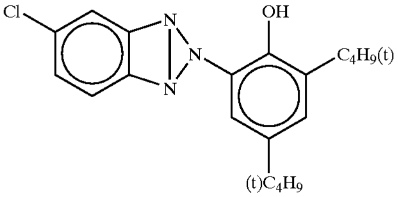
U-4
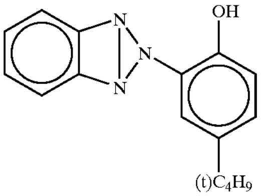
U-5
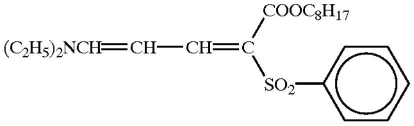
S-1
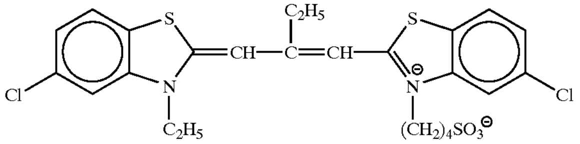
S-2
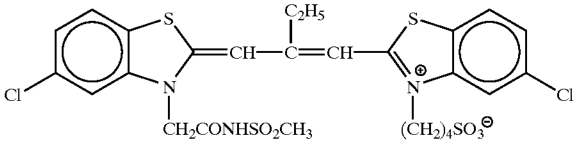
S-3
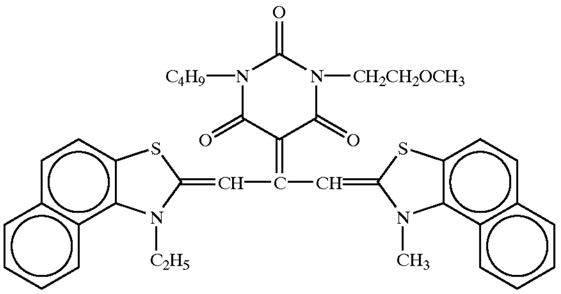
S-4
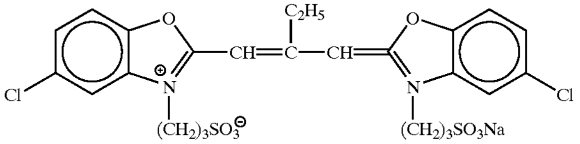
-continued
S-5
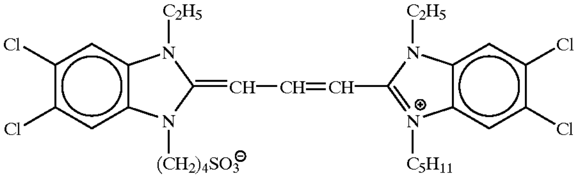
S-6
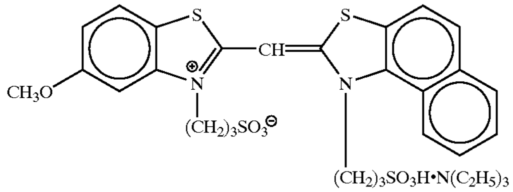
S-7
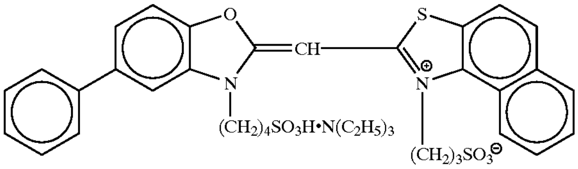
S-8
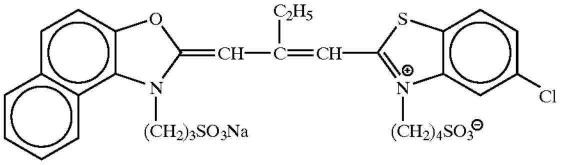
S-9
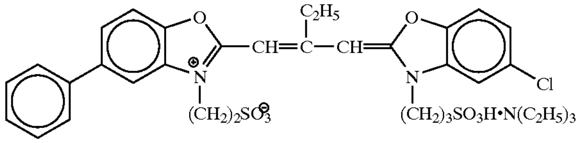
D-1
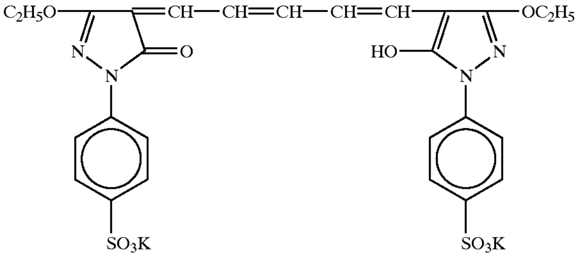
D-2
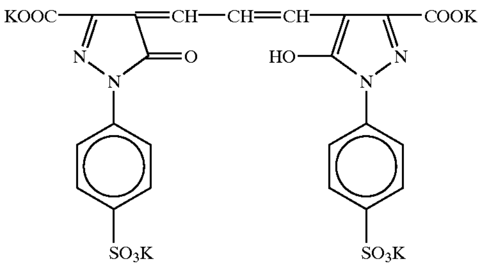

-continued
D-3
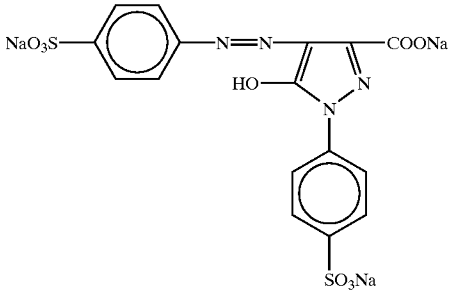
D-4
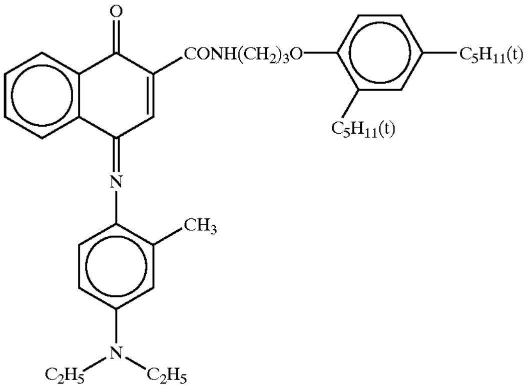
D-5
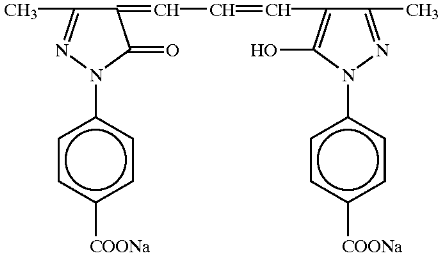
D-6
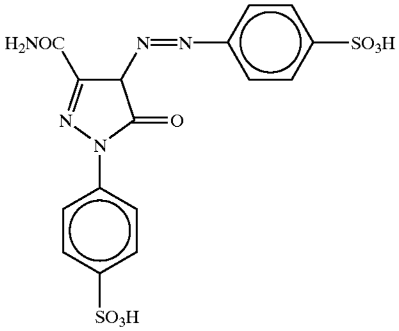
E-1
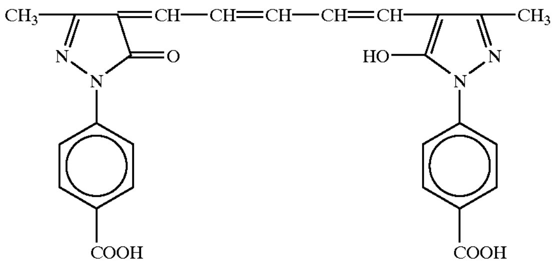
-continued
E-2
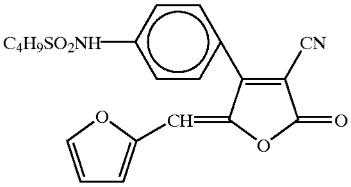
H-1
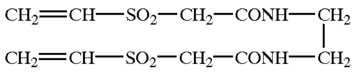
W-1
$C_8F_{17}SO_2NHCH_2CH_2CH_2OCH_2CH_2\overset{\oplus}{N}(CH_3)_3$
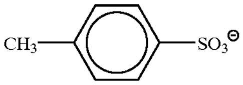
W-2
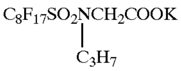
W-3
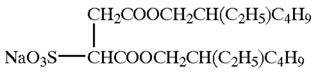
W-4
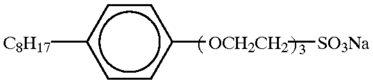
W-5
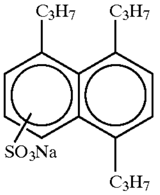
W-6
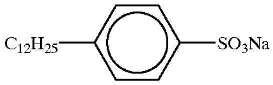
P-1
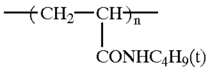
(n = an integer)
M-1
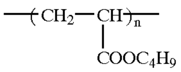
(n = an integer)
F-1
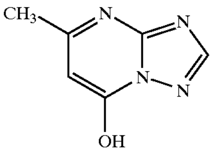
F-2
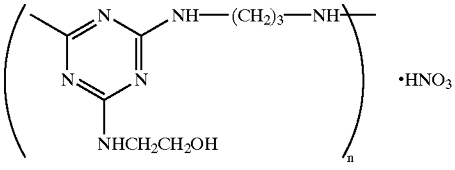
(n = 3 ~ 4)

-continued

F-3

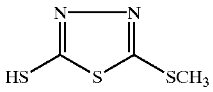

F-4

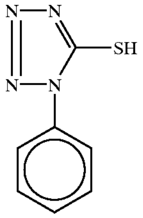

F-5

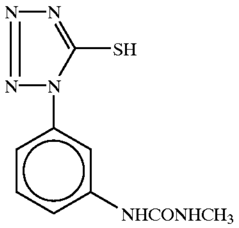

F-6

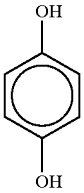

F-7

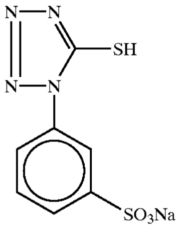

F-8

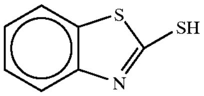

F-2

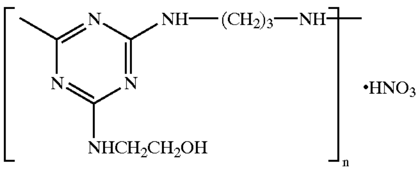

(n = 3 ~ 4)

F-3

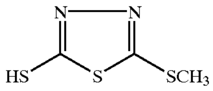

-continued

F-4

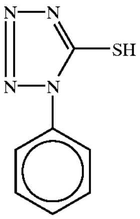

F-5

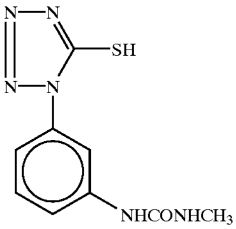

F-6

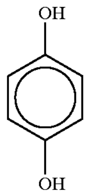

F-7

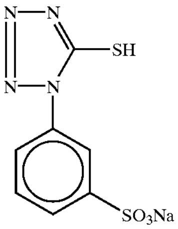

F-8

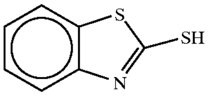

Preparation of Sample Nos. 302 to 305

Sample Nos. 302 to 305 were prepared in the same manner as the Preparation of Sample No. 301 except that the compound of the present invention or comparative compound was to the ninth layer of each sample as shown in Table 7.

TABLE 7

| Sample No. | Compound according to the Invention: Kind | Compound according to the Invention: Amount Added* (mol) | Storage Stability of Latent Image | Change in Dmax with the Lapse of Time |
|---|---|---|---|---|
| 301 (Comparison) | — | — | +0.10 | −0.25 |
| 302 (Comparison) | Comparative Compound E | 2 × $10^{-2}$ | +0.03 | −0.38 |
| 303 (Comparison) | Comparative Compound E | 4 × $10^{-4}$ | +0.10 | −0.28 |
| 304 (Invention) | 1 | 2 × $10^{-2}$ | +0.03 | −0.35 |
| 305 (Invention) | 1 | 4 × $10^{-4}$ | +0.04 | −0.25 |

*mol number per mol of the silver halide in the emulsion layer

Comparative Compound E

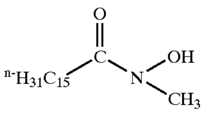

Each sample obtained was cut in strips.

Evaluation of Fluctuation in Photographic Characteristics from Photographing Until Development Processing After each sample was wedgewise exposed by white light, one sample was allowed to stand under conditions of 45° C., 55% RH for 7 days, and the other was stored in a freezer, then each sample was development processed according to the following processing step.

With each sample, the change in the density at the exposure amount of the magenta image of the sample stored in a freezer giving the density of minimum density+1.5 was compared, and (the density of the sample after being stored at 45° C.) minus (the density of the sample after being stored in a freezer) was determined and this was taken as the criterion of the evaluation of the fluctuation in photographic characteristics from photographing until development processing of a photographic material, that is, the storage stability of a latent image. The smaller the value, the larger is the improving effect of the storage stability of the latent image.

Change in Maximum Color Density with the Lapse of Time

One of each sample was allowed to stand at 55° C., 55% RH for 10 days and the other was stored in a freezer and subjected to the same exposure and development processing as above, and the difference in maximum color densities (Dmax) of the green-sensitive layer was determined.

$$\Delta(Dmax)=(Dmax\ after\ raw\ stock)-(Dmax\ after\ frozen\ stock)$$

The results obtained are shown in Table 7.

As can be seen from the results in Table 7, the compound of the present invention shows the sufficient effect of improving storage stability of a latent image with a reduced addition amount and change in maximum color density due to storage is less.

Concerning Comparative Compound E, maximum color density with the lapse of time lowers with the increase of the addition amount, this is presumably because the radical of Comparative Compound E generated by capturing the organic radical in the photographic material accelerates the growth of a dimer of a 4-equivalent magenta coupler (C-7).

Using Sample No. 301 after exposure and an automatic processor, the development processing was conducted according to the development processing step shown below after processing until the cumulative replenishment amount of each tank reached 3 times of the tank capacity.

| Processing Step | Processing Time | Processing Temperature (° C.) | Tank Capacity (liter) | Replenishment Rate (ml/m²) |
|---|---|---|---|---|
| First Development | 4 min | 38 | 12 | 1,000 |
| First Washing | 45 sec | 38 | 2 | 2,200 |
| Reversal | 45 sec | 38 | 2 | 500 |
| Color Development | 4 min | 38 | 12 | 1,000 |
| Bleaching | 3 min | 38 | 4 | 200 |
| Fixing | 3 min | 38 | 8 | 500 |
| Second Washing (1) | 1 min | 38 | 2 | — |
| Second Washing (2) | 1 min | 38 | 2 | 1,100 |
| Stabilization | 1 min | 25 | 2 | 500 |
| Drying | 1 min | 65 | — | — |

Replenishment of the second washing was conducted in a countercurrent system by introducing the replenisher into second washing (2) and introducing the overflow from second washing (2) into second washing (1).

The composition of each processing solution is as follows.

| | Tank Solution | Replenisher |
|---|---|---|
| First Developing Solution | | |
| Pentasodium Nitrilo-N,N,N-trimethylenephosphonate | 2.0 g | 3.0 g |
| Sodium Sulfite | 30 g | 40 g |
| Potassium Hydroquinone Monosulfonate | 30 g | 40 g |
| Potassium Carbonate | 40 g | 48 g |
| 1-Phenyl-4-methyl-4-hydroxymethyl-3-pyrazolidone | 2.0 g | 3.5 g |
| Potassium Bromide | 2.5 g | 0 g |
| Potassium Thiocyanate | 1.2 g | 1.8 g |
| Potassium Iodide | 2.0 mg | — |
| Water to make | 1,000 ml | 1,000 ml |
| pH (adjusted wlth sulfuric acid or potassium hydroxide) | 10.00 | 10.20 |
| First Washing Water | | |
| Ethylenediaminetetramethylene-phosphonic Acid | 2.0 g | Replenisher equals tank solution |
| Disodium Phosphate | 5.0 g | |
| Water to make | 1,000 ml | |
| pH (adjusted with hydrochloric acid or sodium hydroxide) | 7.00 | |
| Reversal Solution | | |
| Pentasodium Nitrilo-N,N,N-trimethylenephosphonate | 3.0 g | Replenisher equals tank solution |
| Stannous Chloride.Dihydrate | 1.0 g | |
| p-Aminophenol | 0.1 g | |
| Sodium Hydroxide | 8 g | |
| Glacial Acetic Acid | 15 ml | |
| Water to make | 1,000 ml | |
| pH (adjusted with acetic acid or sodium hydroxide) | 6.00 | |
| Color Developing Solution | | |
| Pentasodium Nitrilo-N,N,N-trimethylenephosphonate | 2.0 g | 3.0 g |
| Sodium Sulfite | 7.0 g | 10.0 g |
| Trisodium Phosphate.Dodecahydrate | 40 g | 45 g |
| Potassium Bromide | 1.0 g | — |
| Potassium Iodide | 90 mg | — |
| Sodium Hydroxide | 3.0 g | 3.0 g |
| Citrazinic Acid | 1.5 g | 1.5 g |
| N-Ethyl-N-(β-methanesulfonamido-ethyl)-3-methyl-4-aminoaniline. | 15 g | 20 g |

-continued

| | Tank Solution | Replenisher |
|---|---|---|
| 3/2 Sulfate.Monohydrate | | |
| 3,6-Dithiaoctane-1,8-diol | 1.0 g | 1.2 g |
| Water to make | 1,000 ml | 1,000 ml |
| pH (adjusted with sulfuric acid or potassium hydroxide) | 12.00 | 12.20 |
| Bleaching Solution | | |
| Ammonium 1,3-Diaminepropane-tetraacetato Ferrate Monohydrate | 50 g | 100 g |
| Potassium Bromide | 100 g | 200 g |
| Ammonium Nitrate | 10 g | 20 g |
| Acetic Acid (90%) | 60 g | 120 g |
| 3-Mercapto-1,2,4-triazole | 0.0005 mol | 0.0008 mol |
| Water to make | 1,000 ml | 1,000 ml |
| pH (adjusted with nitric acid or aqueous ammonia) | 4.5 | 4.0 |
| Fixing Solution | | |
| Disodium Ethylenediamine-tetraacetate Dihydrate | 10.0 g | 15.0 g |
| Ammonium Thiosulfate | 150 g | 200 g |
| Sodium Sulfite | 25.0 g | 30.0 g |
| Water to make | 1,000 ml | 1,000 ml |
| pH (adjusted with acetic acid or aqueous ammonia) | 6.60 | 6.80 |

Second Washing Water (Both Tank Solution and Replenisher)

City water was passed through a mixed bed column packed with an H-type strongly acidic cation exchange resin (Amberlite IR-120B of Rohm & Haas) and an OH-type anion exchange resin (Amberlite IR-400 of Rohm & Haas) and treated so as to reduce the calcium ion and magnesium ion concentrations to 3 mg/liter or less, subsequently 20 mg/liter of sodium isocyanurate dichloride and 1.5 g/liter of sodium sulfate were added thereto. The pH of this washing water was in the range of from 6.5 to 7.5.

| Stabilizing Solution | Tank Solution | Replenisher |
|---|---|---|
| 1-Hydroxymethyl-1,2,4-triazole | 2.3 g | Replenisher equals tank solution |
| Polyoxyethylene-p-monononylphenyl Ether (average polymerization degree: 10) | 0.3 g | |
| 1,2,4-Triazole | 2.0 g | |
| 1,4-Bis(1,2,4-triazol-1-ylmethyl)-piperazine | 0.2 g | |
| 1,2-Benzisothiazolin-3-one | 0.05 g | |
| Water to make | 1,000 ml | |
| pH (adjusted with sodium hydroxide and acetic acid) | 6.5 | |

EXAMPLE 4

Preparation of Sample Nos. 401 to 404

Sample Nos. 401 to 404 were prepared in the same manner as the preparation of Sample No. 101 in Example 1, except that Comparative Compounds F and G were added to the ninth layer of Sample No. 101 as shown in Table 8.

TABLE 8

| | Compound according to the Invention | | Storage Stability of Latent Image | |
|---|---|---|---|---|
| Sample No. | Kind | Amount Added* (mol) | Green-Sensitive Layer | Blue-Sensitive Layer |
| 101 (Comparison) | — | — | +0.15 | +0.03 |
| 104 (Invention) | 2 | $5 \times 10^{-3}$ | +0.03 | +0.03 |
| 105 (Invention) | 2 | $1 \times 10^{-4}$ | +0.03 | +0.03 |
| 401 (Comparison) | Comparative Compound F | $5 \times 10^{-3}$ | +0.03 | −0.09 |
| 402 (Comparison) | Comparative Compound F | $1 \times 10^{-4}$ | +0.03 | −0.04 |
| 108 (Invention) | 22 | $5 \times 10^{-3}$ | +0.04 | +0.03 |
| 109 (Invention) | 22 | $1 \times 10^{-4}$ | +0.08 | +0.03 |
| 403 (Comparison) | Comparative Compound G | $5 \times 10^{-3}$ | +0.04 | +0.07 |
| 404 (Comparison) | Comparative Compound G | $1 \times 10^{-4}$ | +0.07 | −0.02 |

*) mole number per mol of the silver halide in the emulsion layer

Comparative Compound F (Compound disclosed in JP-1A-59-198453)

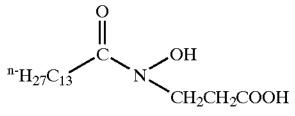

Comparative Compound G (Compound disclosed in JP-A-3-293666)

TABLE 8-continued

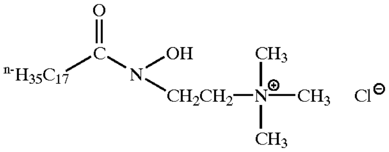

The storage stability of a latent image (fluctuation in photographic characteristics from photographing until development processing) of each of the thus-obtained samples was evaluated in the same manner as in Example 1 together with Sample Nos. 101, 104, 105, 108 and 109 in Example 1.

After each sample was wedgewise exposed by white light, one sample was allowed to stand under conditions of 50° C., 58% RH for 8 days, and the other was stored in a freezer, then each sample was development processed according to the processing step in Example 1.

With each sample, the change in the density at the exposure amount of the magenta image and the yellow image of the sample stored in a freezer giving the density of minimum density +1.0 was compared, and (the density of the sample after being stored at 50° C.) minus (the density of the sample after being stored in a freezer) was determined.

As can be seen from the results in Table 8, Compounds 2 and 22 according to the present invention can not only improve the storage stability of the latent image of the green-sensitive layers where they are added with a reduced addition amount but also exert no influence on the blue-sensitive layers. On the contrary, Comparative Compounds F and G have the effect on the layers where they are added but reduce the density of the blue-sensitive layers, therefore, they are not desirable from the color balance with the green-sensitive layer. Accordingly, the compound of the present invention can exert an influence selectively on an arbitrary emulsion layer with a reduced addition amount.

While the invention has been described in detail and with reference to specific examples thereof, it will be apparent to one skilled in the art that various changes and modifications can be made therein without departing from the spirit and scope thereof.

What is claimed is:

1. A compound represented by formula (VI):

(VI)

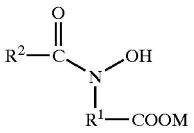

wherein $R^2$ represents a straight chain alkyl group having from 14 to 23 carbon atoms, a substituted aryl group having the sum total of from 20 to 50 carbon atoms, or a substituted alkyl group having the sum total of from 14 to 40 carbon atoms; $R^1$ represents an unsubstituted alkylene group having from 1 to 3 carbon atoms; and M represents a hydrogen atom or a metal atom.

* * * * *